US007611882B2

(12) United States Patent
Bjørnvad et al.

(10) Patent No.: US 7,611,882 B2
(45) Date of Patent: Nov. 3, 2009

(54) **DETERGENT COMPOSITIONS COMPRISING *BACILLUS SUBTILIS* PECTATE LYASES**

(75) Inventors: Mads Eskelund Bjørnvad, Frederiksberg (DK); Martin Schülein, Copenhagen (DK); Torben Henriksen, legal representative, Copenhagen (DK); Vibeke Skovgaard Nielsen, Bagsvaerd (DK); Johan Smets, Lubeek (BE); Carsten Andersen, Værløse (DK); Thomas Thisted, Frederikssund (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 10/478,840

(22) PCT Filed: May 14, 2002

(86) PCT No.: PCT/DK02/00315

§ 371 (c)(1),
(2), (4) Date: Mar. 18, 2005

(87) PCT Pub. No.: WO02/092741

PCT Pub. Date: Nov. 21, 2002

(65) Prior Publication Data

US 2006/0165613 A1    Jul. 27, 2006

Related U.S. Application Data

(60) Provisional application No. 60/290,738, filed on May 14, 2001.

(30) Foreign Application Priority Data

May 14, 2001    (DK)    ............................... 2001 00755

(51) Int. Cl.
C11D 3/00    (2006.01)
C12N 9/88    (2006.01)
C02F 3/34    (2006.01)
(52) U.S. Cl. .................. 435/232; 435/200; 435/262; 510/320
(58) Field of Classification Search ................. 510/320; 435/232, 262, 252.31, 320.1
See application file for complete search history.

(56) References Cited

U.S. PATENT DOCUMENTS 6,172,030 B1    1/2001    Wada et al.
6,399,351 B1    6/2002    Bjornvad et al.
6,808,915 B2 *    10/2004    Schroder Glad et al. ..... 435/232

FOREIGN PATENT DOCUMENTS

| JP | 11-318443 | 11/1999 |
| JP | 2000262292 A | * 9/2000 |
| WO | WO 98/06809 | 2/1998 |
| WO | WO 98/45393 | 10/1998 |
| WO | WO 99/27083 | 6/1999 |
| WO | WO 99/27084 | 6/1999 |
| WO | WO 00/29560 | 5/2000 |
| WO | WO 00/37627 | 6/2000 |
| WO | WO 00/42145 | 7/2000 |
| WO | WO 00/42155 | 7/2000 |
| WO | WO 00/55309 | 9/2000 |
| WO | WO 00/60063 | 10/2000 |
| WO | WO 02/06442 | 1/2002 |

OTHER PUBLICATIONS

Nasser et al., Febs 13343, Part 3, vol. 333, pp. 319-326 (1993).
Kim et al., Bioscience Biotechnology Biochem, Part 5, vol. 58, pp. 947-949 (1994).
Nasser et al., Biochimie, Part 9, vol. 72, pp. 689-696 (1990).
Abstract of Tatsuji et al., Bioscience Biotechnology Biochem, Part 2, vol. 58, pp. 353-358 (1994).
JP Application No. 2000-262292 (Sep. 26, 2000) (abstract and translation).
Abstract of JP Application No. 2000-253888 (Sep. 19, 2000).
Abstract of JP Application No. 11318443 (Nov. 24, 1999).
Abstract of JP 2000-659159.
Nasser et al., Database Biosis, Accession No. PREV199497088806 (1993).
Kim et al., Database CAPLUS, Accession No. 1994:550110 (1994).
Nasser et al., Database Biosis, Accession No. PREV199191043359 (1991).
Sakamoto et al., Database Biosis, Accession No. PREV199497268686 (1994).
Kim et al., Biosci. Biotechn, Biochem. vol. 58, No. 5, pp. 947-949 (1994).
Kim et al., Protein Engineering, vol. 14, No. 5, pp. 343-347 (2001).
Sakamoto et al., Biosci. Biotech Biochem., vol. 58, No. 2, pp. 353-358 (1994).

* cited by examiner

*Primary Examiner*—Nashaat T Nashed
*Assistant Examiner*—Iqbal H Chowdhury
(74) *Attorney, Agent, or Firm*—Elias Lambiris

(57) ABSTRACT

Detergent composition comprising a surfactant and a pectate lyase (EC 4.2.2.2) enzyme en-coded by a DNA sequence endogeneous to a strain of *Bacillus subtilis* or a stabilized variant thereof provides superior cleaning and stain removal.

9 Claims, No Drawings

SEQUENCE LISTING

```
<160> NUMBER OF SEQ ID NOS: 19

<210> SEQ ID NO 1
<211> LENGTH: 1200
<212> TYPE: DNA
<213> ORGANISM: Bacillus subtilis
<220> FEATURE:
<221> NAME/KEY: CDS
<222> LOCATION: (1)..(1200)

<400> SEQUENCE: 1 gct gat tta ggc cac cag acg tta gaa tca aat gat ggc tgg ggc gcg      48
Ala Asp Leu Gly His Gln Thr Leu Glu Ser Asn Asp Gly Trp Gly Ala
1               5                   10                  15 tac tcg acc ggc aca aca ggc gga tca aaa gct tcg tca tcc cac gtg      96
Tyr Ser Thr Gly Thr Thr Gly Gly Ser Lys Ala Ser Ser Ser His Val
                20                  25                  30 tat acc gtc agc aac aga aac cag ctt gtc tcg gca tta ggc aag gac      144
Tyr Thr Val Ser Asn Arg Asn Gln Leu Val Ser Ala Leu Gly Lys Asp
            35                  40                  45
```

```
acc aac aca acg cca aaa atc att tat att aag gga acg att gac atg    192
Thr Asn Thr Thr Pro Lys Ile Ile Tyr Ile Lys Gly Thr Ile Asp Met
        50                  55                  60 aac gtc gat gac aat ctg aag ccg ctt ggt cta aat gat tat aaa gat    240
Asn Val Asp Asp Asn Leu Lys Pro Leu Gly Leu Asn Asp Tyr Lys Asp
65                  70                  75                  80 cca gag tac gat ttg gac aaa tat ttg aaa gcc tat gac cct agc aca    288
Pro Glu Tyr Asp Leu Asp Lys Tyr Leu Lys Ala Tyr Asp Pro Ser Thr
                    85                  90                  95 tgg ggc aaa aag gag ccg tcg ggg aca cta gaa gag gcg aga gca cga    336
Trp Gly Lys Lys Glu Pro Ser Gly Thr Leu Glu Glu Ala Arg Ala Arg
                100                 105                 110 tct cag aaa aat caa aaa gca cga gtc atg gtg gat att ccg gca aac    384
Ser Gln Lys Asn Gln Lys Ala Arg Val Met Val Asp Ile Pro Ala Asn
            115                 120                 125 acg acg atc gtc ggt tca ggg aca aat gcc aaa atc gtg ggc gga aat    432
Thr Thr Ile Val Gly Ser Gly Thr Asn Ala Lys Ile Val Gly Gly Asn
130                 135                 140 ttc cag atc aag agt gat aat gtc atc atc cgc aac atc gaa ttc cag    480
Phe Gln Ile Lys Ser Asp Asn Val Ile Ile Arg Asn Ile Glu Phe Gln
145                 150                 155                 160 gat gct tat gat tat ttt ccg caa tgg gat ccg act gac ggc agc tca    528
Asp Ala Tyr Asp Tyr Phe Pro Gln Trp Asp Pro Thr Asp Gly Ser Ser
                    165                 170                 175 gga aac tgg aac tca caa tac gac aac atc aca ata aac ggc ggc acg    576
Gly Asn Trp Asn Ser Gln Tyr Asp Asn Ile Thr Ile Asn Gly Gly Thr
                180                 185                 190 cat ata tgg att gat cat tgt aca ttt aat gac ggt tcc cgt ccg gac    624
His Ile Trp Ile Asp His Cys Thr Phe Asn Asp Gly Ser Arg Pro Asp
            195                 200                 205 agc aca tcg cca aag tat ttc ggc aga aaa tat cag cac cat gac ggc    672
Ser Thr Ser Pro Lys Tyr Phe Gly Arg Lys Tyr Gln His His Asp Gly
        210                 215                 220 caa acc gat gct tct aac ggc gct aac tat atc acg atg tct tac aac    720
Gln Thr Asp Ala Ser Asn Gly Ala Asn Tyr Ile Thr Met Ser Tyr Asn
225                 230                 235                 240 tat tat cac gat cat gat aaa agc tcc att ttc gga tca agc gac agc    768
Tyr Tyr His Asp His Asp Lys Ser Ser Ile Phe Gly Ser Ser Asp Ser
                    245                 250                 255 aaa aca tct gat gac ggc aaa tta aaa atc acg ctc cat cat aac cgc    816
Lys Thr Ser Asp Asp Gly Lys Leu Lys Ile Thr Leu His His Asn Arg
                260                 265                 270 tat aaa aat atc gtc cag cgc gca ccg aga gtc cgc ttc ggg cag gtg    864
Tyr Lys Asn Ile Val Gln Arg Ala Pro Arg Val Arg Phe Gly Gln Val
            275                 280                 285 cac gtt tac aac aac tat tat gaa ggc agc aca agc tcc tcg gat tat    912
His Val Tyr Asn Asn Tyr Tyr Glu Gly Ser Thr Ser Ser Ser Asp Tyr
        290                 295                 300 gcc ttc agc tat gcg tgg gga atc gga aaa tca tct aaa atc tac gct    960
Ala Phe Ser Tyr Ala Trp Gly Ile Gly Lys Ser Ser Lys Ile Tyr Ala
305                 310                 315                 320 caa aac aat gtc att gac gtg cct gga ctg tca gcc gct aaa acg atc   1008
Gln Asn Asn Val Ile Asp Val Pro Gly Leu Ser Ala Ala Lys Thr Ile
                    325                 330                 335 agc gta ttc agc ggg gga acg gct tta tat gac tca ggc aca ttg ctg   1056
Ser Val Phe Ser Gly Gly Thr Ala Leu Tyr Asp Ser Gly Thr Leu Leu
                340                 345                 350 aat ggc acg cag atc aac gca tcg gct gca aac ggg ctg agt tct tct   1104
Asn Gly Thr Gln Ile Asn Ala Ser Ala Ala Asn Gly Leu Ser Ser Ser
            355                 360                 365
```

```
gtc ggc tgg aca ccg tct ctg cac ggc aca atc gat gct tcc gcg cat    1152
Val Gly Trp Thr Pro Ser Leu His Gly Thr Ile Asp Ala Ser Ala His
370                 375                 380 gta aaa tcg aat gtt ata tct caa gcg ggt gcg ggt aaa tta aat taa    1200
Val Lys Ser Asn Val Ile Ser Gln Ala Gly Ala Gly Lys Leu Asn
385                 390                 395
```

<210> SEQ ID NO 2
<211> LENGTH: 399
<212> TYPE: PRT
<213> ORGANISM: Bacillus subtilis

<400> SEQUENCE: 2

```
Ala Asp Leu Gly His Gln Thr Leu Glu Ser Asn Asp Gly Trp Gly Ala
1               5                   10                  15

Tyr Ser Thr Gly Thr Thr Gly Gly Ser Lys Ala Ser Ser Ser His Val
            20                  25                  30

Tyr Thr Val Ser Asn Arg Asn Gln Leu Val Ser Ala Leu Gly Lys Asp
        35                  40                  45

Thr Asn Thr Thr Pro Lys Ile Ile Tyr Ile Lys Gly Thr Ile Asp Met
50                  55                  60

Asn Val Asp Asp Asn Leu Lys Pro Leu Gly Leu Asn Asp Tyr Lys Asp
65                  70                  75                  80

Pro Glu Tyr Asp Leu Asp Lys Tyr Leu Lys Ala Tyr Asp Pro Ser Thr
                85                  90                  95

Trp Gly Lys Lys Glu Pro Ser Gly Thr Leu Glu Glu Ala Arg Ala Arg
            100                 105                 110

Ser Gln Lys Asn Gln Lys Ala Arg Val Met Val Asp Ile Pro Ala Asn
        115                 120                 125

Thr Thr Ile Val Gly Ser Gly Thr Asn Ala Lys Ile Val Gly Gly Asn
130                 135                 140

Phe Gln Ile Lys Ser Asp Asn Val Ile Ile Arg Asn Ile Glu Phe Gln
145                 150                 155                 160

Asp Ala Tyr Asp Tyr Phe Pro Gln Trp Asp Pro Thr Asp Gly Ser Ser
                165                 170                 175

Gly Asn Trp Asn Ser Gln Tyr Asp Asn Ile Thr Ile Asn Gly Gly Thr
            180                 185                 190

His Ile Trp Ile Asp His Cys Thr Phe Asn Asp Gly Ser Arg Pro Asp
        195                 200                 205

Ser Thr Ser Pro Lys Tyr Phe Gly Arg Lys Tyr Gln His His Asp Gly
210                 215                 220

Gln Thr Asp Ala Ser Asn Gly Ala Asn Tyr Ile Thr Met Ser Tyr Asn
225                 230                 235                 240

Tyr Tyr His Asp His Asp Lys Ser Ser Ile Phe Gly Ser Ser Asp Ser
                245                 250                 255

Lys Thr Ser Asp Asp Gly Lys Leu Lys Ile Thr Leu His His Asn Arg
            260                 265                 270

Tyr Lys Asn Ile Val Gln Arg Ala Pro Arg Val Arg Phe Gly Gln Val
        275                 280                 285

His Val Tyr Asn Asn Tyr Tyr Glu Gly Ser Thr Ser Ser Ser Asp Tyr
290                 295                 300

Ala Phe Ser Tyr Ala Trp Gly Ile Gly Lys Ser Ser Lys Ile Tyr Ala
305                 310                 315                 320

Gln Asn Asn Val Ile Asp Val Pro Gly Leu Ser Ala Ala Lys Thr Ile
                325                 330                 335
```

```
Ser Val Phe Ser Gly Gly Thr Ala Leu Tyr Asp Ser Gly Thr Leu Leu
            340                 345                 350

Asn Gly Thr Gln Ile Asn Ala Ser Ala Ala Asn Gly Leu Ser Ser Ser
        355                 360                 365

Val Gly Trp Thr Pro Ser Leu His Gly Thr Ile Asp Ala Ser Ala His
    370                 375                 380

Val Lys Ser Asn Val Ile Ser Gln Ala Gly Ala Gly Lys Leu Asn
385                 390                 395

<210> SEQ ID NO 3
<211> LENGTH: 6661
<212> TYPE: DNA
<213> ORGANISM: artificial sequence
<220> FEATURE:
<223> OTHER INFORMATION: plasmid pMOL995

<400> SEQUENCE: 3
gaattcctta gtgctttcat agattaaact cacatcacgc tttaaatcgc ttattttaga      60
ctttaaagac ttgttttctt caagcaactc attataatca tttacatttt cattaaatcg     120
ctctacaaga ccactatatt tttctttaac ttgcccatgt tctttactta attttttata     180
ttctctcgcc atatcagtac tcatgagatt ctaacatgc tgttttaacc tatcgttatc      240
tctcgcagca gtcactaagt ttttataatc acgctccgat ataacaacat ttttggttgg     300
tttcttttct gttttcatta tttctttttcc caaaccaaac atggactttt cacccgttgg    360
cacttcaaca cttttcatgt gtcgtttcgc tggtacttct aaatctgatt taactttatc    420
gctataagca gtccattcat cttttttaac tgctaaattt ttttctagaa atcaatctc    480 ttttccaaa gtttgttttt taaatttagc tgtctcaata tgtttacggt cagagccacg     540
ttcaccacgc ttcaactcaa aaccctgttt tttcatatgc tcgggaatt tatcttgtag     600 ccataacagt tcttgacgat taaacacatt tttttccttgc agttttccat cacgcatagg   660
cacaacacct aaatgcatgt gaggggtttg ctcatcatta tgaactgttg cataagcaat   720
attttgcttg ccatatcgtt cggaaaataa tttataactt tcctcaaaaa atcgtttttg   780
ttctcctgga tccagttgct caaaaaaatc tcggtcagat gttactagca actcatttac    840
aagaacagca tctttcctcg ttttttcttgt acctgttttt tgtgattcaa taatttctttt 900 gacacgttcg ttgtaatcaa tatttttatc atttttcaaa tcataatttt cacgtgttcg   960
ctcatggtca atatcatcat tcgttctact ttttcgctct ctttgattat gaaattgcat   1020
gccttttagt ccagctgatt tcacttttg cattctacaa actgcataac tcatatgtaa   1080
atcgctcctt tttaggtggc acaaatgtga ggcattttcg ctctttccgg caaccacttc   1140
caagtaaagt ataacacact atactttata ttcataaagt gtgtgctctg cgaggctgtc   1200
ggcagtgccg accaaaacca taaacccttt aagccctttc tttttttttac gagaaaaaag   1260 aaacaaaaaa acctgccctc tgccacctca gcaagggggg gttttgctct cgtgctcgtt    1320 taaaatcag caagggacag gtagtatttt ttgagaagat cactcaaaaa atctccacct    1380 ttaaacccctt gccaattttt attttgtccg ttttgtctag cttaccgaaa gccagactca   1440
gcaagaataa aatttttatt gtctttcggt tttctagtgt aacggacaaa accactcaaa   1500
ataaaaaaga tacaagagag gtctctcgta tcttttattc agcaatcgcg cccgattgct    1560
gaacagatta ataatagatt ttagcttttt atttgttgaa aaaagctaat caaattgttg   1620
tcgggatcaa ttactgcaaa gtctcgttca tcccaccact gatctttaa tgatgtattg    1680
```

```
gggtgcaaaa tgcccaaagg cttaatatgt tgatataatt catcaattcc ctctacttca   1740
atgcggcaac tagcagtacc agcaataaac gactccgcac ctgtacaaac cggtgaatca   1800
ttactacgag agcgccagcc ttcatcactt gcctcccata gatgaatccg aacctcatta   1860
cacattagaa ctgcgaatcc atcttcatgg tgaaccaaag tgaaacctag tttatcgcaa   1920
taaaaaccta tactctttt aatatccccg actggcaatg ccggggcggc cgacatacat    1980
tcgctttgcc ccaccgggtc cgtctgttat taatgccgcc aaacctgaat tgcaaccga    2040 gctgtcgcct tcccttgtcc agccgacaat gtcatggtgg tcgaaataat catgctgtgc   2100
tccgtacgca tactgttttc tcgcttttaa gatcggttca atttgtgtt tcaaggcagg    2160 aatttcgcgc tgggagtctc ctttcgtccc gtacatatcc ccgtagaaaa cctgagggta   2220
tccagattcc cttgtgagaa taaaagcgta agcaagcggc ttaaaccatg tttgacagt    2280 cgaccccttc cctcttatcc aacctttatt gcttcaccca aaccgaaacg gaccctccat   2340
taacagagaa attaccccat ccgtctgcat taattgtgac ggtgcctgtc ctatttccgg   2400
taatatctct ccaaacttgt cccgctttat ttttccccac atacatccat ttgttaccac   2460
ctggaccatc tgcataatg gtggcaaggc ctgaatttgg atgggagcta tttccctctc    2520
ttgtccaacc gataatatca tgatgatcaa agtaatcatg ctgcgtacca taggcaaaag   2580
tttgacgtgc ctgcagaaga gggtctattt tagatttcat agccggaaca ccatgggttg   2640
ggataccgta gtaatcccca taaaatacgg aaggataacc ttgttccctt gtcagaacca   2700
atgcatatgc aagtggttta aaccattgtt gaacaaagga ttccaatgct tccccgggct   2760
gagaatcatg gttatcaaca aaagtaacgg catgtgttgg atgttttgc accacagaac    2820 catttaaaat atttctcata tcataataac caccgctatt agatgcattg tacaaattat   2880
agtggagagg aacatcaaac accgagtgat tccaacttgt tttattcaaa tagttttcaa   2940
ttgcaccaag gtcattttc caaaactcag ccactgcaaa cattggttta cctgtggtgt    3000
tacgcacatg tgtaagccaa tctctcgtaa agctatattt tatatgtttc actgcatcta   3060
ttctaaatcc atcaaggttc agtgtattcg tataccacac tccccagttt ctaagttcat   3120
gtattacttc tgggtgatcc atatccacgt ctgcatacat aagatagtca tagttgccat   3180
tctctgtatc gacttcccag tcccaggcct tgcctgttcc cctgaattta tatattttgt   3240
tttgaagctg gcgtgactga tcccaatctg tcccatcaaa atgataccag cgccacttaa   3300
agctggaatg gttatttcct cttccaggaa aatcaaactt tgtccacgct tctattgcat   3360
actctcctga ggtttcctgg tttcggttgc tccgattcac ttctaccgca tttacaattt   3420
ccgtaccatc tgctccacct ttatgattca tgacgacatc accatatacc tgaatgccgt   3480 tatttttaa agaggtcacc gcagcctgta gctggttgcg tgttccatat tttgtacgaa   3540
ccgtcccctt ctggttaaac tctccaagat catataaatc ataggctcca taacctacat   3600
cattctggga agtcccttc catgcaggtg ggatccatac agctgttatc cctttactct    3660
ttaagttagc tgcgtcatcc ctcaacctgt tccaatgatt cccgtcattt ggcaaatacc   3720
attcgaaata ttgcatcata gtaccatttg ttccattatg atgggccgcg gatgttttg    3780 taatcggcaa actgacaaat aacagcgtgc acataagcac aagtctgaac gaaactgtcc   3840
gctttcgttt ttgaatcatg tttcctctcc ctctcatttt cttatacaaa ttatatttta   3900
catatcagta aaataataac aacccccctt tattccttat ttttacacag cggacagtct   3960
ggacagcata aaaaatacccc tgtctgatga cagacaaggt atttttatgg tcttcttctt   4020
ttctcaaaca atcgatccac ttcttcagcc aaatcatcag tcatcaagag ctcccgggat   4080
```

```
agactgtaac attctcacgc ataaaatccc ctttcatttt ctaatgtaaa tctattaccT    4140
tattattaat tcaattcgct cataattaat ccttttcctt attacgcaaa atggcccgat    4200
ttaagcacac cctttattcc gttaatgcgc catgacagcc atgataatta ctaatactag    4260
gagaagttaa taaatacgta accaacatga ttaacaatta ttagaggtca tcgttcaaaa    4320
tggtatgcgt tttgacacat ccactatata tccgtgtcgt tctgtccact cctgaatccc    4380
attccagaaa ttctctagcg attccagaag tttctcagag tcggaaagtt gaccagacat    4440
tacgaactgg cacagatggt cataacctga aggaagatct gattgcttaa ctgcttcagt    4500
taagaccgaa gcgctcgtcg tataacagat gcgatgatgc agaccaatca acatggcacc    4560
tgccattgct acctgtacag tcaaggatgg tagaaatgtt gtcggtcctt gcacacgaat    4620
attacgccat ttgcctgcat attcaaacag ctcttctacg ataagggcac aaatcgcatc    4680
gtggaacgtt tgggcttcta ccgatttagc agtttgatac actttctcta agtatccacc    4740
tgaatcataa atcggcaaaa tagagaaaaa ttgaccatgt gtaagcggcc aatctgattc    4800
cacctgagat gcataatcta gtagaatctc ttcgctatca aaattcactt ccaccttcca    4860
ctcaccggtt gtccattcat ggctgaactc tgcttcctct gttgacatga cacacatcat    4920
ctcaatatcc gaatagggcc catcagtctg acgaccaaga gagccataaa caccaatagc    4980
cttaacatca tccccatatt tatccaatat tcgttcctta atttcatgaa caatcttcat    5040
tctttcttct ctagtcatta ttattggtcc attcactatt ctcattccct tttcagataa    5100
ttttagattt gcttttctaa ataagaatat ttggagagca ccgttcttat tcagctatta    5160
ataactcgtc ttcctaagca tccttcaatc cttttaataa caattatagc atctaatctt    5220
caacaaactg gcccgtttgt tgaactactc tttaataaaa taattttcc gttcccaatt    5280
ccacattgca ataatagaaa atccatcttc atcggctttt tcgtcatcat ctgtatgaat    5340
caaatcgcct tcttctgtgt catcaaggtt taatttttta tgtatttctt ttaacaaacc    5400
accataggag attaaccttt tacggtgtaa accttcctcc aaatcagaca acgtttcaa    5460
attcttttct tcatcatcgg tcataaaatc cgtatccttt acaggatatt ttgcagtttc    5520
gtcaattgcc gattgtatat ccgatttata tttatttttc ggtcgaatca tttgaacttt    5580
tacatttgga tcatagtcta atttcattgc cttttccaa aattgaatcc attgttttg    5640
attcacgtag ttttctgtat tcttaaaata agttggttcc acacatacca atacatgcat    5700
gtgctgatta taagaattat ctttattatt tattgtcact tccgttgcac gcataaaacc    5760
aacaagattt ttattaattt ttttatattg catcattcgg cgaaatcctt gagccatatc    5820
tgacaaactc ttatttaatt cttcgccatc ataaacattt ttaactgtta atgtgagaaa    5880
caaccaacga actgttggct tttgtttaat aacttcagca acaaccttt gtgactgaat    5940
gccatgtttc attgctctcc tccagttgca cattggacaa agcctggatt tacaaaacca    6000
cactcgatac aactttcttt cgcctgtttc acgattttgt ttatactcta atatttcagc    6060
acaatctttt actctttcag cctttttaaa ttcaagaata tgcagaagtt caaagtaatc    6120
aacattagcg attttctttt ctctccatgg tctcacttt ccactttttg tcttgtccac    6180
taaaaccctt gattttcat ctgaataaat gctactatta ggacacataa tattaaaga    6240
aaccccatc tatttagtta tttgtttagt cacttataac tttaacagat ggggttttc    6300
tgtgcaacca attttaaggg ttttcaatac tttaaaacac atacatacca acacttcaac    6360
gcacctttca gcaactaaaa taaaaatgac gttatttcta tatgtatcaa gataagaaag    6420
```

```
aacaagttca aaaccatcaa aaaaagacac cttttcaggt gcttttttta ttttataaac    6480
tcattccctg atctcgactt cgttcttttt ttacctctcg gttatgagtt agttcaaatt    6540
cgttcttttt aggttctaaa tcgtgttttt cttggaattg tgctgtttta tcctttacct    6600
tgtctacaaa ccccttaaaa acgtttttaa aggcttttaa gccgtctgta cgttccttaa    6660
g                                                                   6661
```

```
<210> SEQ ID NO 4
<211> LENGTH: 39
<212> TYPE: DNA
<213> ORGANISM: artificial sequence
<220> FEATURE:
<223> OTHER INFORMATION: Primer A

<400> SEQUENCE: 4
cattctgcag ccgcggcagc tgatttaggc caccagacg                           39

<210> SEQ ID NO 5
<211> LENGTH: 44
<212> TYPE: DNA
<213> ORGANISM: artificial sequence
<220> FEATURE:
<223> OTHER INFORMATION: Primer B

<400> SEQUENCE: 5
gtacctcgcg agtcgacttc ttaatttaat ttacccgcac ccgc                     44

<210> SEQ ID NO 6
<211> LENGTH: 1200
<212> TYPE: DNA
<213> ORGANISM: Bacillus subtilis
<220> FEATURE:
<221> NAME/KEY: CDS
<222> LOCATION: (1)..(1200)

<400> SEQUENCE: 6 gct gat tta ggc cac cag acg ttg gga tcc aat gat ggc tgg ggc gcg    48
Ala Asp Leu Gly His Gln Thr Leu Gly Ser Asn Asp Gly Trp Gly Ala
1               5                   10                  15 tac tcg acc ggc acg aca ggc gga tca aaa gca tcc tcc tca aat gtg    96
Tyr Ser Thr Gly Thr Thr Gly Gly Ser Lys Ala Ser Ser Ser Asn Val
            20                  25                  30 tat acc gtc agc aac aga aac cag ctt gtc tcg gca tta ggg aag gaa   144
Tyr Thr Val Ser Asn Arg Asn Gln Leu Val Ser Ala Leu Gly Lys Glu
        35                  40                  45 acg aac aca acg cca aaa atc att tat atc aag gga acg att gac atg   192
Thr Asn Thr Thr Pro Lys Ile Ile Tyr Ile Lys Gly Thr Ile Asp Met
    50                  55                  60 aac gtg gat gac aat ctg aag ccg ctt ggc cta aat gac tat aaa gat   240
Asn Val Asp Asp Asn Leu Lys Pro Leu Gly Leu Asn Asp Tyr Lys Asp
65                  70                  75                  80 ccg gag tat gat ttg gac aaa tat ttg aaa gcc tat gat cct agc aca   288
Pro Glu Tyr Asp Leu Asp Lys Tyr Leu Lys Ala Tyr Asp Pro Ser Thr
                85                  90                  95 tgg ggc aaa aaa gag ccg tcg gga aca caa gaa gaa gcg aga gca cgc   336
Trp Gly Lys Lys Glu Pro Ser Gly Thr Gln Glu Glu Ala Arg Ala Arg
            100                 105                 110 tct cag aaa aac caa aaa gca cgg gtc atg gtg gat atc cct gca aac   384
Ser Gln Lys Asn Gln Lys Ala Arg Val Met Val Asp Ile Pro Ala Asn
        115                 120                 125 acg acg atc gtc ggt tca ggg act aac gct aaa gtc gtg gga gga aac   432
Thr Thr Ile Val Gly Ser Gly Thr Asn Ala Lys Val Val Gly Gly Asn
```

-continued

```
              130                 135                 140
ttc caa atc aag agt gat aac gtc att att cgc aac att gaa ttc cag    480
Phe Gln Ile Lys Ser Asp Asn Val Ile Ile Arg Asn Ile Glu Phe Gln
145                 150                 155                 160 gat gcc tat gac tat ttt ccg caa tgg gat ccg act gac gga agc tca    528
Asp Ala Tyr Asp Tyr Phe Pro Gln Trp Asp Pro Thr Asp Gly Ser Ser
                165                 170                 175 ggg aac tgg aac tca caa tac gac aac atc acg ata aac ggc ggc aca    576
Gly Asn Trp Asn Ser Gln Tyr Asp Asn Ile Thr Ile Asn Gly Gly Thr
            180                 185                 190 cac atc tgg att gat cac tgt aca ttt aat gac ggt tcg cgt ccg gac    624
His Ile Trp Ile Asp His Cys Thr Phe Asn Asp Gly Ser Arg Pro Asp
        195                 200                 205 agc aca tca ccg aaa tat tat gga aga aaa tat cag cac cat gac ggc    672
Ser Thr Ser Pro Lys Tyr Tyr Gly Arg Lys Tyr Gln His His Asp Gly
    210                 215                 220 caa acg gat gct tcc aac ggt gct aac tat atc acg atg tcc tac aac    720
Gln Thr Asp Ala Ser Asn Gly Ala Asn Tyr Ile Thr Met Ser Tyr Asn
225                 230                 235                 240 tat tat cac gat cat gat aaa agc tcc att ttc gga tca agt gac agc    768
Tyr Tyr His Asp His Asp Lys Ser Ser Ile Phe Gly Ser Ser Asp Ser
                245                 250                 255 aaa acc tcc gat gac ggc aaa tta aaa att acg ctg cat cat aac cgc    816
Lys Thr Ser Asp Asp Gly Lys Leu Lys Ile Thr Leu His His Asn Arg
            260                 265                 270 tat aaa aat att gtc cag cgc gcg ccg aga gtc cgc ttc ggg caa gtg    864
Tyr Lys Asn Ile Val Gln Arg Ala Pro Arg Val Arg Phe Gly Gln Val
        275                 280                 285 cac gta tac aac aac tat tat gaa gga agc aca agc tct tca agt tat    912
His Val Tyr Asn Asn Tyr Tyr Glu Gly Ser Thr Ser Ser Ser Ser Tyr
    290                 295                 300 cct ttt agc tat gca tgg gga atc gga aag tca tct aaa atc tat gcc    960
Pro Phe Ser Tyr Ala Trp Gly Ile Gly Lys Ser Ser Lys Ile Tyr Ala
305                 310                 315                 320 caa aac aat gtc att gac gta ccg gga ctg tca gct gct aaa acg atc   1008
Gln Asn Asn Val Ile Asp Val Pro Gly Leu Ser Ala Ala Lys Thr Ile
                325                 330                 335 agc gta ttc agc ggg gga acg gct tta tat gac tcc ggc acg ttg ctg   1056
Ser Val Phe Ser Gly Gly Thr Ala Leu Tyr Asp Ser Gly Thr Leu Leu
            340                 345                 350 aac ggc aca cag atc aac gca tcg gct gca aac ggg ctg agc tct tct   1104
Asn Gly Thr Gln Ile Asn Ala Ser Ala Ala Asn Gly Leu Ser Ser Ser
        355                 360                 365 gtc ggc tgg acg ccg tct ctg cat gga tcg att gat gct tct gct aat   1152
Val Gly Trp Thr Pro Ser Leu His Gly Ser Ile Asp Ala Ser Ala Asn
    370                 375                 380 gtg aaa tca aat gtt ata aat caa gcg ggt gcg ggt aaa tta aat taa   1200
Val Lys Ser Asn Val Ile Asn Gln Ala Gly Ala Gly Lys Leu Asn
385                 390                 395
```

<210> SEQ ID NO 7
<211> LENGTH: 399
<212> TYPE: PRT
<213> ORGANISM: Bacillus subtilis

<400> SEQUENCE: 7

```
Ala Asp Leu Gly His Gln Thr Leu Gly Ser Asn Asp Gly Trp Gly Ala
1               5                   10                  15

Tyr Ser Thr Gly Thr Thr Gly Gly Ser Lys Ala Ser Ser Ser Asn Val
            20                  25                  30
```

```
Tyr Thr Val Ser Asn Arg Asn Gln Leu Val Ser Ala Leu Gly Lys Glu
             35                  40                  45

Thr Asn Thr Thr Pro Lys Ile Ile Tyr Ile Lys Gly Thr Ile Asp Met
 50                  55                  60

Asn Val Asp Asp Asn Leu Lys Pro Leu Gly Leu Asn Asp Tyr Lys Asp
 65                  70                  75                  80

Pro Glu Tyr Asp Leu Asp Lys Tyr Leu Lys Ala Tyr Asp Pro Ser Thr
                 85                  90                  95

Trp Gly Lys Lys Glu Pro Ser Gly Thr Gln Glu Glu Ala Arg Ala Arg
                100                 105                 110

Ser Gln Lys Asn Gln Lys Ala Arg Val Met Val Asp Ile Pro Ala Asn
            115                 120                 125

Thr Thr Ile Val Gly Ser Gly Thr Asn Ala Lys Val Val Gly Gly Asn
130                 135                 140

Phe Gln Ile Lys Ser Asp Asn Val Ile Ile Arg Asn Ile Glu Phe Gln
145                 150                 155                 160

Asp Ala Tyr Asp Tyr Phe Pro Gln Trp Asp Pro Thr Asp Gly Ser Ser
                165                 170                 175

Gly Asn Trp Asn Ser Gln Tyr Asp Asn Ile Thr Ile Asn Gly Gly Thr
            180                 185                 190

His Ile Trp Ile Asp His Cys Thr Phe Asn Asp Gly Ser Arg Pro Asp
            195                 200                 205

Ser Thr Ser Pro Lys Tyr Tyr Gly Arg Lys Tyr Gln His His Asp Gly
            210                 215                 220

Gln Thr Asp Ala Ser Asn Gly Ala Asn Tyr Ile Thr Met Ser Tyr Asn
225                 230                 235                 240

Tyr Tyr His Asp His Asp Lys Ser Ser Ile Phe Gly Ser Ser Asp Ser
                245                 250                 255

Lys Thr Ser Asp Asp Gly Lys Leu Lys Ile Thr Leu His His Asn Arg
            260                 265                 270

Tyr Lys Asn Ile Val Gln Arg Ala Pro Arg Val Arg Phe Gly Gln Val
            275                 280                 285

His Val Tyr Asn Asn Tyr Tyr Glu Gly Ser Thr Ser Ser Ser Ser Tyr
            290                 295                 300

Pro Phe Ser Tyr Ala Trp Gly Ile Gly Lys Ser Ser Lys Ile Tyr Ala
305                 310                 315                 320

Gln Asn Asn Val Ile Asp Val Pro Gly Leu Ser Ala Ala Lys Thr Ile
                325                 330                 335

Ser Val Phe Ser Gly Gly Thr Ala Leu Tyr Asp Ser Gly Thr Leu Leu
            340                 345                 350

Asn Gly Thr Gln Ile Asn Ala Ser Ala Ala Asn Gly Leu Ser Ser Ser
            355                 360                 365

Val Gly Trp Thr Pro Ser Leu His Gly Ser Ile Asp Ala Ser Ala Asn
            370                 375                 380

Val Lys Ser Asn Val Ile Asn Gln Ala Gly Ala Gly Lys Leu Asn
385                 390                 395

<210> SEQ ID NO 8
<211> LENGTH: 42
<212> TYPE: DNA
<213> ORGANISM: artificial sequence
<220> FEATURE:
<223> OTHER INFORMATION: Primer C

<400> SEQUENCE: 8
```

-continued gtcgccgggg cggccgctat caattggtaa ctgtatctca gc    42

<210> SEQ ID NO 9
<211> LENGTH: 64
<212> TYPE: DNA
<213> ORGANISM: artificial sequence
<220> FEATURE:
<223> OTHER INFORMATION: Primer D

<400> SEQUENCE: 9
gtcgcccggg agctctgatc aggtaccaag cttgtcgacc tgcagaatga ggcagcaaga    60
agat    64

<210> SEQ ID NO 10
<211> LENGTH: 61
<212> TYPE: DNA
<213> ORGANISM: artificial sequence
<220> FEATURE:
<223> OTHER INFORMATION: Primer E

<400> SEQUENCE: 10
gtcggcggcc gctgatcacg taccaagctt gtcgacctgc agaatgaggc agcaagaaga    60
t    61

<210> SEQ ID NO 11
<211> LENGTH: 35
<212> TYPE: DNA
<213> ORGANISM: artificial sequence
<220> FEATURE:
<223> OTHER INFORMATION: Primer F

<400> SEQUENCE: 11
gtcggagctc tatcaattgg taactgtatc tcagc    35

<210> SEQ ID NO 12
<211> LENGTH: 35
<212> TYPE: DNA
<213> ORGANISM: artificial sequence
<220> FEATURE:
<223> OTHER INFORMATION: Primer G

<400> SEQUENCE: 12
aacagctgat cacgactgat cttttagctt ggcac    35

<210> SEQ ID NO 13
<211> LENGTH: 37
<212> TYPE: DNA
<213> ORGANISM: artificial sequence
<220> FEATURE:
<223> OTHER INFORMATION: Primer H

<400> SEQUENCE: 13
aactgcagcc gcggcacatc ataatgggac aaatggg    37

<210> SEQ ID NO 14
<211> LENGTH: 39
<212> TYPE: DNA
<213> ORGANISM: artificial sequence
<220> FEATURE:
<223> OTHER INFORMATION: Primer J

<400> SEQUENCE: 14
cattctgcag ccgcggcagc tgatttaggc caccagacg    39

<210> SEQ ID NO 15
<211> LENGTH: 46
<212> TYPE: DNA
<213> ORGANISM: artificial sequence
<220> FEATURE:
<223> OTHER INFORMATION: Primer K

<400> SEQUENCE: 15
gtacctcgcg agcggccgct tcttaattta atttacccgc acccgc        46

<210> SEQ ID NO 16
<211> LENGTH: 39
<212> TYPE: DNA
<213> ORGANISM: artificial sequence
<220> FEATURE:
<223> OTHER INFORMATION: Primer L

<400> SEQUENCE: 16
cattctgcag ccgcggcagc tgatttaggc caccagacg        39

<210> SEQ ID NO 17
<211> LENGTH: 46
<212> TYPE: DNA
<213> ORGANISM: artificial sequence
<220> FEATURE:
<223> OTHER INFORMATION: Primer M

<400> SEQUENCE: 17
gtacctcgcg agcggccgct tcttaattta atttacccgc acccgc        46

<210> SEQ ID NO 18
<211> LENGTH: 1200
<212> TYPE: DNA
<213> ORGANISM: Bacillus subtilis
<220> FEATURE:
<221> NAME/KEY: CDS
<222> LOCATION: (1)..(1200)

<400> SEQUENCE: 18

| gct | gat | tta | ggc | cac | cag | acg | tta | ggg | tca | aat | gat | ggc | tgg | ggc | gcg | 48 |
| Ala | Asp | Leu | Gly | His | Gln | Thr | Leu | Gly | Ser | Asn | Asp | Gly | Trp | Gly | Ala | |
| 1 | | | | 5 | | | | | 10 | | | | | 15 | | |

| tac | tcg | acc | ggc | acg | aca | ggc | gga | tca | aaa | gca | tcg | tcc | tcg | aac | gtg | 96 |
| Tyr | Ser | Thr | Gly | Thr | Thr | Gly | Gly | Ser | Lys | Ala | Ser | Ser | Ser | Asn | Val | |
| | | | 20 | | | | | 25 | | | | | 30 | | | |

| tat | acc | gtc | agc | aac | aga | aac | caa | ctt | gtc | tct | gca | tta | ggc | aag | aaa | 144 |
| Tyr | Thr | Val | Ser | Asn | Arg | Asn | Gln | Leu | Val | Ser | Ala | Leu | Gly | Lys | Lys | |
| | | | 35 | | | | | 40 | | | | | 45 | | | |

| acg | gat | acg | acg | cct | aaa | atc | att | tac | atc | aag | ggt | gcg | att | gac | atg | 192 |
| Thr | Asp | Thr | Thr | Pro | Lys | Ile | Ile | Tyr | Ile | Lys | Gly | Ala | Ile | Asp | Met | |
| | 50 | | | | | 55 | | | | | 60 | | | | | |

| aat | gtt | gat | gac | aat | ctg | aag | ccg | ctt | gac | gca | gat | gat | tat | gct | gac | 240 |
| Asn | Val | Asp | Asp | Asn | Leu | Lys | Pro | Leu | Asp | Ala | Asp | Asp | Tyr | Ala | Asp | |
| 65 | | | | | 70 | | | | | 75 | | | | | 80 | |

| cca | gag | tac | gat | ttg | aac | aaa | tat | tta | aaa | gct | tat | gat | cca | agc | aca | 288 |
| Pro | Glu | Tyr | Asp | Leu | Asn | Lys | Tyr | Leu | Lys | Ala | Tyr | Asp | Pro | Ser | Thr | |
| | | | | 85 | | | | | 90 | | | | | 95 | | |

| tgg | ggc | aaa | aaa | gag | cct | tcc | ggc | aca | cag | gaa | gaa | gcc | aga | gaa | cgt | 336 |
| Trp | Gly | Lys | Lys | Glu | Pro | Ser | Gly | Thr | Gln | Glu | Glu | Ala | Arg | Glu | Arg | |
| | | | 100 | | | | | 105 | | | | | 110 | | | |

| tct | caa | aaa | aac | caa | aaa | gca | aga | gtg | atg | gtt | gac | att | cct | gcg | aat | 384 |
| Ser | Gln | Lys | Asn | Gln | Lys | Ala | Arg | Val | Met | Val | Asp | Ile | Pro | Ala | Asn | |
| | | 115 | | | | | 120 | | | | | 125 | | | | |

-continued

```
aca acg att gtc ggt tca ggg aca aat gcc aaa atc gtg ggc gga aac      432
Thr Thr Ile Val Gly Ser Gly Thr Asn Ala Lys Ile Val Gly Gly Asn
    130                 135                 140 ttc caa atc aag agt gat aat gtc atc atc cgc aac atc gaa ttc caa      480
Phe Gln Ile Lys Ser Asp Asn Val Ile Ile Arg Asn Ile Glu Phe Gln
145                 150                 155                 160 gat gct tat gac tat ttt ccg caa tgg gac ccg act gac ggt agc tca      528
Asp Ala Tyr Asp Tyr Phe Pro Gln Trp Asp Pro Thr Asp Gly Ser Ser
                165                 170                 175 gga aac tgg aac tca caa tat gac aac atc aca ata aac ggc ggc acg      576
Gly Asn Trp Asn Ser Gln Tyr Asp Asn Ile Thr Ile Asn Gly Gly Thr
            180                 185                 190 cat ata tgg att gac cat tgc aca ttt aat gac gga tcc cgt cct gac      624
His Ile Trp Ile Asp His Cys Thr Phe Asn Asp Gly Ser Arg Pro Asp
        195                 200                 205 agt aca tca cca aag tat tac gga aga gaa tat cag cat cat gac ggc      672
Ser Thr Ser Pro Lys Tyr Tyr Gly Arg Glu Tyr Gln His His Asp Gly
    210                 215                 220 caa aca gat gct tct aac ggc gcc aac tat atc acg atg tct tac aac      720
Gln Thr Asp Ala Ser Asn Gly Ala Asn Tyr Ile Thr Met Ser Tyr Asn
225                 230                 235                 240 tat tat cac gat cat gat aaa agc tcc att ttc gga tca agc gac agc      768
Tyr Tyr His Asp His Asp Lys Ser Ser Ile Phe Gly Ser Ser Asp Ser
                245                 250                 255 aaa acc tcc gat gat ggc aaa tta aaa att acg ctt cac cat aac cgc      816
Lys Thr Ser Asp Asp Gly Lys Leu Lys Ile Thr Leu His His Asn Arg
            260                 265                 270 tac aaa aat atc gtt cag cgc gca ccg aga gtc cgc ttc ggg caa gtg      864
Tyr Lys Asn Ile Val Gln Arg Ala Pro Arg Val Arg Phe Gly Gln Val
        275                 280                 285 cac gta tac aac aac tat tat gaa ggc agc aaa agc tca tcc gga tat      912
His Val Tyr Asn Asn Tyr Tyr Glu Gly Ser Lys Ser Ser Ser Gly Tyr
    290                 295                 300 gct ttc agt tat gca tgg gga atc ggc aag tca tct aaa atc tat gct      960
Ala Phe Ser Tyr Ala Trp Gly Ile Gly Lys Ser Ser Lys Ile Tyr Ala
305                 310                 315                 320 caa aac aat gtc att gac gta ccg gga ctg tca gct gag aaa aca atc     1008
Gln Asn Asn Val Ile Asp Val Pro Gly Leu Ser Ala Glu Lys Thr Ile
                325                 330                 335 agc gtg ttt aaa ggt gga acg gct tta tat gac tca ggc aca ttg ctg     1056
Ser Val Phe Lys Gly Gly Thr Ala Leu Tyr Asp Ser Gly Thr Leu Leu
            340                 345                 350 aat ggc acg cgg atc agc gca tca gct gca aac ggg ctg agc tct tct     1104
Asn Gly Thr Arg Ile Ser Ala Ser Ala Ala Asn Gly Leu Ser Ser Ser
        355                 360                 365 gtc ggc tgg aca cca tct ctc cac ggc aca atc gat gat tcc gcg aat     1152
Val Gly Trp Thr Pro Ser Leu His Gly Thr Ile Asp Asp Ser Ala Asn
    370                 375                 380 gtg aaa tcg aat gtt ata tcc caa gcg ggt gcg ggt aaa tta aat taa     1200
Val Lys Ser Asn Val Ile Ser Gln Ala Gly Ala Gly Lys Leu Asn
385                 390                 395

<210> SEQ ID NO 19
<211> LENGTH: 399
<212> TYPE: PRT
<213> ORGANISM: Bacillus subtilis

<400> SEQUENCE: 19

Ala Asp Leu Gly His Gln Thr Leu Gly Ser Asn Asp Gly Trp Gly Ala
1               5                   10                  15
```

```
Tyr Ser Thr Gly Thr Thr Gly Gly Ser Lys Ala Ser Ser Asn Val
         20                  25                  30

Tyr Thr Val Ser Asn Arg Asn Gln Leu Val Ser Ala Leu Gly Lys Lys
             35                  40                  45

Thr Asp Thr Thr Pro Lys Ile Ile Tyr Ile Lys Gly Ala Ile Asp Met
    50                  55                  60

Asn Val Asp Asp Asn Leu Lys Pro Leu Asp Ala Asp Tyr Ala Asp
65                  70                  75                  80

Pro Glu Tyr Asp Leu Asn Lys Tyr Leu Lys Ala Tyr Asp Pro Ser Thr
                85                  90                  95

Trp Gly Lys Lys Glu Pro Ser Gly Thr Gln Glu Ala Arg Glu Arg
            100                 105                 110

Ser Gln Lys Asn Gln Lys Ala Arg Val Met Val Asp Ile Pro Ala Asn
        115                 120                 125

Thr Thr Ile Val Gly Ser Gly Thr Asn Ala Lys Ile Val Gly Gly Asn
    130                 135                 140

Phe Gln Ile Lys Ser Asp Asn Val Ile Ile Arg Asn Ile Glu Phe Gln
145                 150                 155                 160

Asp Ala Tyr Asp Tyr Phe Pro Gln Trp Asp Pro Thr Asp Gly Ser Ser
                165                 170                 175

Gly Asn Trp Asn Ser Gln Tyr Asp Asn Ile Thr Ile Asn Gly Gly Thr
            180                 185                 190

His Ile Trp Ile Asp His Cys Thr Phe Asn Asp Gly Ser Arg Pro Asp
        195                 200                 205

Ser Thr Ser Pro Lys Tyr Tyr Gly Arg Glu Tyr Gln His His Asp Gly
    210                 215                 220

Gln Thr Asp Ala Ser Asn Gly Ala Asn Tyr Ile Thr Met Ser Tyr Asn
225                 230                 235                 240

Tyr Tyr His Asp His Asp Lys Ser Ser Ile Phe Gly Ser Ser Asp Ser
                245                 250                 255

Lys Thr Ser Asp Asp Gly Lys Leu Lys Ile Thr Leu His His Asn Arg
            260                 265                 270

Tyr Lys Asn Ile Val Gln Arg Ala Pro Arg Val Arg Phe Gly Gln Val
        275                 280                 285

His Val Tyr Asn Asn Tyr Glu Gly Ser Lys Ser Ser Ser Gly Tyr
    290                 295                 300

Ala Phe Ser Tyr Ala Trp Gly Ile Gly Lys Ser Ser Lys Ile Tyr Ala
305                 310                 315                 320

Gln Asn Asn Val Ile Asp Val Pro Gly Leu Ser Ala Glu Lys Thr Ile
                325                 330                 335

Ser Val Phe Lys Gly Gly Thr Ala Leu Tyr Asp Ser Gly Thr Leu Leu
            340                 345                 350

Asn Gly Thr Arg Ile Ser Ala Ser Ala Ala Asn Gly Leu Ser Ser Ser
        355                 360                 365

Val Gly Trp Thr Pro Ser Leu His Gly Thr Ile Asp Asp Ser Ala Asn
    370                 375                 380

Val Lys Ser Asn Val Ile Ser Gln Ala Gly Ala Gly Lys Leu Asn
385                 390                 395
```

DETERGENT COMPOSITIONS COMPRISING *BACILLUS SUBTILIS* PECTATE LYASES

CROSS-REFERENCE TO RELATED APPLICATIONS

This application is a 35 U.S.C. 371 national application of PCT/DK02/00315 filed May 14, 2002, which claims priority or the benefit under 35 U.S.C. 119 of Danish application no. PA 2001 00755 filed May 14, 2001 and U.S. provisional application No. 60/290,738 filed May 14, 2001, the contents of which are fully incorporated herein by reference.

The present invention relates to a detergent composition comprising a pectate lyase enzyme (EC 4.2.2.2) isolated from a strain of *Bacillus subtilis*, preferably a pectate lyase enzyme cloned from a strain of *Bacillus subtilis* or a stabilized variant thereof, to the pectate lyase enzyme encoded by the DNA sequence present in the plasmid of the strain *Bacillus subtilis*, DSM 14218, a *Bacillus* expression vector and a method for producing the pectate lyase in a *Bacillus* host cell.

BACKGROUND OF THE INVENTION

Pectin polymers are important constituents of plant cell walls. Pectin is a hetero-polysaccharide with a backbone composed of alternating homogalacturonan (smooth regions) and rhamnogalacturonan (hairy regions). The smooth regions are linear polymers of 1,4-linked alpha-D-galacturonic acid. The galacturonic acid residues can be methyl-esterified on the carboxyl group to a varying degree, usually in a non-random fashion with blocks of polygalacturonic acid being completely methyl-esterified.

Pectinases can be classified according to their preferential substrate, highly methyl-esterified pectin or low methyl-esterified pectin and polygalacturonic acid (pectate), and their reaction mechanism, beta-elimination or hydrolysis. Pectinases can be mainly endo-acting, cutting the polymer at random sites within the chain to give a mixture of oligomers, or they may be exo-acting, attacking from one end of the polymer and producing monomers or dimers. Several pectinase activities acting on the smooth regions of pectin are included in the classification of enzymes provided by the Enzyme Nomenclature (1992) such as pectate lyase (EC 4.2.2.2), pectin lyase (EC 4.2.2.10), polygalacturonase (EC 3.2.1.15), exo-polygalacturonase (EC 3.2.1.67), exo-polygalacturonate lyase (EC 4.2.2.9) and exo-poly-alpha-galacturonosidase (EC 3.2.1.82).

The international patent application published as WO99/27083 discloses a pectate lyase cloned from *Bacillus licheniformis*. The international patent application published as WO99/27084 discloses pectate lyases cloned from *Bacillus agaradhaerens*, *Bacillus halodurans* and other *Bacillus* sp.

Cloning of a pectate lyase from *Bacillus subtilis* has been describe in Nasser et al. (1993) FEBS 335:319-326. This pectate lyase requires divalent cations for maximum activity, calcium ions being the most stimulating.

JP 2000-262292A discloses a gene coding for *Bacillus* protopectinase, a transformant containing the gene, and refinement of fiber using the transformant.

U.S. Pat. No. 6,172,030 discloses a detergent composition containing a *Bacillus* protopectinase having optimum pH 7 or higher against protopectin and polygalacturonic acid substrates.

It is the object of the present invention to provide a pectate lyase enzyme having high performance in detergent compositions.

SUMMARY OF THE INVENTION

The inventors have now found a novel polypeptide having pectate lyase (EC 4.2.2.2) activity and have succeeded in cloning and expressing the pectate lyase enzyme in a *Bacillus* host.

Accordingly, in a first aspect the present invention relates to a detergent composition comprising a surfactant and a pectate lyase (EC 4.2.2.2) enzyme encoded by a DNA sequence endogeneous to a strain of *Bacillus subtilis* or a stabilized variant thereof, preferably a pectate lyase encoded by a DNA sequence obtained from *Bacillus subtilis*, DSM 14218, or a stabilized site-directed variant thereof, such as the polypeptide encoded by a DNA sequence comprising positions 1-1197 of SEQ ID NO: 1 or a stabilized site-directed variant of the pectate lyase enzyme encoded by a DNA sequence comprising positions 1-1197 of SEQ ID NO: 1.

In a second aspect the present invention relates to method of cleaning a fabric, a dishware or hard surface with a detergent composition according to the invention for superior cleaning performance.

In a third aspect, the invention relates to the use of the detergent composition of the invention for fabric cleaning and/or fabric stain removal and/or fabric whiteness maintenance and/or fabric softening and/or fabric colour appearance and/or for cleaning hard surfaces such as floors, walls, bathroom tiles and the like and/or for hand and machine dishwashing and/or for oral and/or dental applications.

In a further aspect, the invention relates to a polypeptide having pectate lyase (EC 4.2.2.2) activity, which is selected from one of (a) a polypeptide encoded by the DNA sequence of positions 1-1197 of SEQ ID NO: 1; (b) a polypeptide produced by culturing a cell comprising the sequence of positions 1-1197 of SEQ ID NO: 1 under conditions wherein the DNA sequence is expressed; and (c) a site-directed variant of the polypeptide of (a) or (b) which has been stabilized by alteration of one, two, three, four or five amino acid residues to other amino acid residues.

In yet further aspects, the invention relates to an enzyme preparation comprising the pectate lyase enzyme of the invention, to an isolated polynucleotide molecule encoding the pectate lyase of the invention, to an expression vector, to a cultured cell capable of expressing the pectate lyase of the invention, and to a method of producing the pectate lyase of the invention.

DETAILED DESCRIPTION OF THE INVENTION

For the purpose of the present invention the term "obtained from" or "obtainable from" as used herein in connection with a specific source, means that the enzyme is produced or can be produced by the specific source, or by a cell in which a gene from the source have been inserted.

The term "wild-type enzyme" denotes an enzyme, which is endogenous to a naturally occurring microorganism such as a fungus or a bacterium found in Nature.

The term "parent enzyme" as used herein means an enzyme in which modifications are being made to produce the enzyme variants of the invention. A parent enzyme may be an enzyme isolated from a natural source, or an enzyme wherein previous modification(s) have been made while retaining the characteristic activity of the enzyme in question. The parent pectate lyase of the invention may be a wild-type pectate lyase.

The term "enzyme variant" means an enzyme comprising differences in its amino acid sequence from that of the parent enzyme. The differences comprise substitutions, deletions and/or insertions as compared to the parent enzyme.

The pectate lyase of the invention may be obtained from a strain of *Bacillus subtilis*.

In a preferred embodiment, the pectate lyase of the invention is obtained from the species *Bacillus subtilis*. The strain *Bacillus subtilis* was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on 5 Apr. 2001 under the deposition number DSM 14218.

In the present context, the term "enzyme preparation" is intended to mean either be a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species; or the fermentation product of a microorganism which acts as a host cell for expression of a recombinant pectate lyase, but which microorganism simultaneously produces other enzymes, e.g. xyloglucanases, proteases, or cellulases, being naturally occurring fermentation products of the microorganism, i.e. the enzyme complex conventionally produced by the corresponding naturally occurring microorganism.

In the present context the term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector is to be introduced. Thus, the vector may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expressed" or "recombinantly expressed" used herein in connection with expression of a polypeptide or protein is defined according to the standard definition in the art. Recombinant expression of a protein is generally performed by using an expression vector as described immediately above.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity (e.g. another polypeptide than the polypeptide of the invention) originating from the homologous cell from which the polypeptide of the invention is originally obtained.

The term "obtained from" as used herein in connection with a specific microbial source, means that the polynucleotide and/or polypeptide produced by the specific source, or by a cell in which a gene from the source have been inserted.

The term "operably linked", when referring to DNA segments, denotes that the segments are arranged so that they function in concert for their intended purposes, e.g. transcription initiates in the promoter and proceeds through the coding segment to the terminator The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "identity" denotes the homology between two amino acid sequences or between two nucleotide sequences. For purposes of the present invention, the degree of identity between two amino acid sequences is determined by a Needleman-Wunsch alignment, useful for both protein and DNA alignments. For protein alignments the default scoring matrix used is BLOSUM50, and the penalty for the first residue in a gap is −12, while the penalty for additional residues in a gap is −2. The alignment may be made with the Align software from the FASTA package version v20u6 (W. R. Pearson and D. J. Lipman (1988), "Improved Tools for Biological Sequence Analysis", PNAS 85:2444-2448; and W. R. Pearson (1990) "Rapid and Sensitive Sequence Comparison with FASTP and FASTA", Methods in Enzymology, 183: 63-98).

The degree of identity between two nucleotide sequences may be determined using the same algorithm and software package as described above using the identity matrix as the default scoring matrix. The penalty for the first residue in a gap is −16, while the penalty for additional residues in a gap is −4.

Enzyme Variant

In the context of this invention, the term "enzyme variant" means an enzyme comprising differences in its amino acid sequence from that of a standard enzyme. The differences comprise substitutions, deletions and/or insertions as compared to the standard enzyme.

In the context of this invention, a specific numbering of amino acid residue positions in cell-wall degrading enzymes, especially pectate lyase enzymes, is employed. For example, by aligning the amino acid sequences of known pectate lyases it is possible to unambiguously allot an amino acid position number to any amino acid residue in any pectate lyase enzyme, if its amino acid sequence is known.

Using the numbering system originating from the amino acid sequence of the pectate lyase encoded by the polynucleotide present in the plasmid of the strain *Bacillus subtilis* DSM 14218, disclosed in SEQ ID NO: 2, aligned with the amino acid sequence of a number of other pectate lyases, it is possible to indicate the position of an amino acid residue in a pectate lyase enzyme unambiguously.

In describing the various pectate lyase enzyme variants produced or contemplated according to this invention, the following nomenclatures are adapted for ease of reference:

Substitutions:

[Original Amino Acid; Position; Substituted Amino Acid]

Accordingly, the substitution of serine with isoleucine in position 72 is designated as S72I.

Multiple mutations are separation by addition marks ("+"), e.g. M169I+F198V, representing mutations in positions 169 and 198 substituting methionine (M) with isoleucine (I), and phenylalanine (F) with valine (V), respectively.

Deletions:

A deletion of glycine in position 195 will be indicated by:
  Gly195* or G195*

Correspondingly the deletion of more than one amino acid residue, such as the deletion of glycine and leucine in positions 195 and 196 will be designated
  Gly195*+Leu196* or G195*+L196*

Insertions:

The insertion of an additional amino acid residue such as e.g. a lysine after G195 is indicated by:
  Gly195GlyLys or G195GK;

or, when more than one amino acid residue is inserted, such as e.g. a Lys and Ala after G195 this will be indicated as:
  Gly195GlyLysAla or G195GKA In such cases the inserted amino acid residue(s) are numbered by the addition of lower case letters to the position number of the amino acid residue preceding the inserted amino acid residue(s). In the above example the sequences 194 to 196 would thus be changed from: 194 195 196
  A-G-L to: 194 195 195a 195b 196
  A-G-K-A-L In cases where an amino acid residue identical to the existing amino acid residue is inserted it is clear that degeneracy in the nomenclature arises. If for example a glycine is inserted after the glycine in the above example this would be indicated by G195GG. The same actual change could just as well be indicated as A194AG for the change from: 194 195 196
  A-G-L to: 194 195 195a 196
  A-G-G-L or 194 194a 195 196

Such instances will be apparent to the skilled person and the indication G195GG and corresponding indications for this type of insertions are thus meant to comprise such equivalent degenerate indications.

All positions referred to herein by pectate lyase numbering refer, unless otherwise stated, to the numbering described above, and are determined relative to the amino acid sequence of the pectate lyase encoded by the polynucleotide present in the plasmid of the strain *Bacillus subtilis* DSM 14218, disclosed in SEQ ID NO:2.

The term "detergent stability" or "storage stability" is intended to mean the stability of the protein in a formulation containing detergents e.g. anionic surfactants. Anionic surfactants are characterized by the combination of an anionic group and a hydrophobic tail. When binding to the protein, a positively charged residue like Lysine or Arginine, and a hydrophobic area are thus likely interaction points. Similarly the dynamic of particularly flexible regions is opening up for the accessibility to amino acids normally buried in the internal of the protein. These residues are typically hydrophobic and are thus attractive for the tail of the surfactant. A chemical interaction between enzyme and surfactant will with high certainty leave the enzyme inactive. Thus improved detergent- or storage stability means that at a certain detergent concentration and temperature, a higher enzymatic activity will be retained after a certain period of time (higher residual activity). Accordingly, thermostability and detergent stability are two independent characteristics of a protein or an enzyme.

Polynucleotides

Within preferred embodiments of the invention an isolated polynucleotide of the invention will hybridize to similar sized regions of SEQ ID NO:1 or a sequence complementary thereto, under at least medium stringency conditions.

In particular polynucleotides of the invention will hybridize to a denatured double-stranded DNA probe comprising either the full sequence shown in SEQ ID NO: 1 or the sequence shown in positions 1-1197 of SEQ ID NO: 1 or any probe comprising a subsequence of SEQ ID NO: 1 having a length of at least about 100 base pairs under at least medium stringency conditions, but preferably at high stringency conditions as described in detail below. Suitable experimental conditions for determining hybridization at medium or high stringency between a nucleotide probe and a homologous DNA or RNA sequence involve presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5× Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6-13), 32P-dCTP-labeled (specific activity higher than 1×109 cpm/μg) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using an X-ray film.

As previously noted, the isolated polynucleotides of the present invention include DNA and RNA. Methods for isolating DNA and RNA are well known in the art. DNA and RNA encoding genes of interest can be cloned in Gene Banks or DNA libraries by means of methods known in the art.

Polynucleotides encoding polypeptides having pectate lyase activity of the invention are then identified and isolated by, for example, hybridization or PCR.

The present invention further provides counterpart polypeptides and polynucleotides from different bacterial strains (orthologs or paralogs). Of particular interest are pectate lyase polypeptides from strains of Bacillus subtilis, exemplified by the strain DSM 14218.

Species homologues of a polypeptide with pectate lyase activity of the invention can be cloned using information and compositions provided by the present invention in combination with conventional cloning techniques. For example, a DNA sequence of the present invention can be cloned using chromosomal DNA obtained from a cell type that expresses the protein. Suitable sources of DNA can be identified by probing Northern blots with probes designed from the sequences disclosed herein. A library is then prepared from chromosomal DNA of a positive cell line. A DNA sequence of the invention encoding an polypeptide having pectate lyase activity can then be isolated by a variety of methods, such as by probing with probes designed from the sequences disclosed in the present specification and claims or with one or more sets of degenerate probes based on the disclosed sequences. A DNA sequence of the invention can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (monoclonal or polyclonal) raised against the pectate lyase cloned from Bacillus subtilis, e.g. from DSM 14218, expressed and purified as described in Materials and Methods and the examples, or by an activity test relating to a polypeptide having pectate lyase activity.

Polypeptides

The sequence of amino acids in positions 1-399 of SEQ ID NO: 2 represents a mature pectate lyase sequence comprising the catalytic active domain of the enzyme of the invention.

The present invention also provides pectate lyase polypeptides that are substantially homologous to the polypeptide of amino acids in position 1-399 of SEQ ID NO: 2 and species homologs (paralogs or orthologs) thereof. The term "substantially homologous" is used herein to denote polypeptides having 98.5%, preferably at least 99%, more preferably at least 99.5%, sequence identity to the sequence shown in amino acids nos. 1-399 of SEQ ID NO: 2 or its orthologs or paralogs. Percent sequence identity is determined by a Needleman-Wunsch alignment as described above.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, protein A (Nilsson et al., EMBO J. 4:1075, 1985; Nilsson et al., Methods Enzymol. 198:3, 1991. See, in general Ford et al., Protein Expression and Purification 2: 95-107, 1991, which is incorporated herein by reference. DNAs encoding affinity tags are available from commercial suppliers (e.g., Pharmacia Biotech, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions to a polypeptide of the invention having pectate lyase activity.

TABLE 1

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the pectate lyase polypeptides of the present invention can be identified according to procedures known in the art, such as site-directed mutagenesis or alanine-scanning mutagenesis (Cunningham and Wells, Science 244: 1081-1085, 1989). In the latter technique, single alanine mutations are introduced at every residue in the molecule, and the resultant mutant molecules are tested for biological activity (i.e pectate lyase activity) to identify amino acid residues that are critical to the activity of the molecule. See also, Hilton et al., *J. Biol. Chem.* 271:4699-4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306-312, 1992; Smith et al., *J. Mol. Biol.* 224:899-904, 1992; Wlodaver et al., *FEBS Lett.* 309:59-64, 1992. The identities of essential amino acids can also be inferred from analysis of homologies with polypeptides related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science* 241: 53-57, 1988), Bowie and Sauer *Proc. Natl. Acad. Sci. USA* 86:2152-2156, 1989), WO95/17413, or WO 95/22625. Briefly, these authors disclose methods for simultaneously randomizing two or more positions in a polypeptide, or recombination/shuffling of different mutations (WO95/17413, WO95/22625), followed by selecting for a functional polypeptide, and then sequencing the mutagenized polypeptides to determine the spectrum of allowable substitutions at each position. Other methods that can be used include phage display (e.g., Lowman et al., *Biochem.* 30:10832-10837, 1991; Ladner et al., U.S. Pat. No. 5,223,409; Huse, WIPO Publication WO 92/06204) and region-directed mutagenesis (Derbyshire et al., *Gene* 46: 145, 1986; Ner et al., *DNA* 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

In a preferred embodiment, the present invention provides a variant enzyme of a pectate lyase endogeneous to *Bacillus subtilis*, DSM 14218, or another strain of *Bacillus subtilis*, the variant being a site directed variant wherein one, two, three, four or five amino acids residues have been altered to other amino acid residues, thereby obtaining a variant enzyme with increased stability in detergent compositions.

Examples of variant enzymes of the pectate lyase of SEQ ID NO:2 include, but are not limited to, those disclosed below in Example 6 and Wash performance example C.

Immunological Cross-Reactivity

Polyclonal antibodies, especially monospecific polyclonal antibodies, to be used in determining immunological cross-reactivity may be prepared by use of a purified enzyme having pectate lyase activity. More specifically, antiserum against the pectate lyase of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27-31). Purified immunoglobulins may be obtained from the antisera, for example by salt precipitation (($NH_4)_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, Ed.), Blackwell Scientific Publications, 1967, pp. 655-706), by crossed immunoelectrophoresis (N. Axelsen et al., supra, Chapters 3 and 4), or by rocket immunoelectrophoresis (N. Axelsen et al., Chapter 2).

The Vector

As described in further detail below, the host of the invention is transformed with a vector comprising a pectate lyase encoding DNA sequence. Preferably, the vector is integrated into the genome of the host, more preferably it has been amplified on the genome.

In another preferred embodiment of the invention, the vector is present as an expression plasmid, preferably as a multicopy plasmid.

The *Bacillus* expression vector of the invention carries an inserted pectate lyase-encoding DNA sequence. Preferably, the expression cassette of the vector comprises regulatory regions from a *Bacillus* sp., more preferably are such regulatory regions endogenous to the host.

Expression of a Pectate Lyase Enzyme

Recombinant Expression Vectors

A recombinant vector comprising a DNA construct encoding the enzyme of the invention may be any vector conveniently subjected to recombinant DNA procedures, and the choice of vector will often depend on the host cell into which it is to be introduced. This introduction of vector into the host cell is often referred to as the transformed host cell. Such transformation indicates introduction of DNA into a host cell by using e.g. protoplasts, natural competent cells, transfection, conjugation, electroporation, or any equivalent method. Thus, the vector may be an autonomously replicating vector, i.e. a vector existing as an extra-chromosomal entity, the replication of which is independent of chromosomal replication, e.g. a plasmid. Alternatively, the vector may be one which, when introduced into a host cell, is integrated into the host cell genome in part or in its entirety and replicated together with the chromosome(s) into which it has been integrated.

The vector is preferably an expression vector in which the DNA sequence encoding the pectate lyase enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the CBD.

The promoter may be any DNA sequence showing transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gen, or the *Bacillus pumilus* xylosidase gene, or the phage Lambda $P_R$ or $P_L$ promoters or the *E. coli* lac, trp or tac promoters. Alternatively, it is possible to design integration vectors such that the DNA encoding the pectate lyase enzyme will only become functionally expressed once it is properly integrated into the host genome, e.g. downstream from a resident promoter.

The DNA sequence encoding the pectate lyase enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct a pectate lyase enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the pectate lyase enzyme in the correct reading frame. Secretory signal sequences are commonly positioned 5' to the DNA sequence encoding the. The secretory signal sequence may be that normally associated with the pectate lyase enzyme or may be from a gene encoding another secreted protein.

The procedures used to ligate the DNA sequences coding for the present pectate lyase enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cells

The cloned DNA molecule introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the cloned DNA molecule or the recombinant vector of the invention is introduced may be any cell capable of producing the desired enzyme and includes bacteria, yeast, fungi and higher eukaryotic cells.

Examples of bacterial host cells which on cultivation may be capable of producing the enzyme of the invention may be a gram-positive bacteria such as a strain of *Bacillus*, in particular *Bacillus alkalophilus, Bacillus amyloliquefaciens, Bacillus brevis, Bacillus lautus, Bacillus lentus, Bacillus licheniformis, Bacillus circulans, Bacillus coagulans, Bacillus megatherium, Bacillus stearothermophilus, Bacillus subtilis* and *Bacillus thuringiensis*, a strain of *Lactobacillus*, a strain of *Streptococcus*, a strain of *Streptomyces*, in particular *Streptomyces lividans* and *Streptomyces murinus*, or the host cell may be a gram-negative bacteria such as a strain of *Escherichia coli*.

The transformation of the bacteria may be effected by protoplast transformation, electroporation, conjugation, or by using competent cells in a manner known per se (cf e.g. Sambrook et al., supra).

When expressing the enzyme in a bacterium such as *Escherichia coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in a gram-positive bacterium such as a strain of *Bacillus* or a strain of *Streptomyces*, the enzyme may be retained in the cytoplasm, or may be directed to the extra-cellular medium by a bacterial secretion sequence.

Examples of a fungal host cell which on cultivation may be capable of producing the enzyme of the invention is e.g. a strain of *Aspergillus* or *Fusarium*, in particular *Aspergillus awamori, Aspergillus nidulans, Aspergillus niger, Aspergillus oryzae*, and *Fusarium oxysporum*, and a strain of *Trichoderma*, preferably *Trichoderma harzianum, Trichoderma reesei* and *Trichoderma viride*.

Fungal cells may be transformed by a process involving protoplast formation and transformation of the protoplasts followed by regeneration of the cell wall in a manner known per se. The use of a strain of *Aspergillus* as a host cell is described in EP 238 023 (Novo Nordisk A/S), the contents of which are hereby incorporated by reference.

Examples of a host cell of yeast origin which on cultivation may be capable of producing the enzyme of the invention is e.g. a strain of *Hansenula* sp., a strain of *Kluyveromyces* sp., in particular *Kluyveromyces lactis* and *Kluyveromyces marcianus*, a strain of *Pichia* sp., a strain of *Saccharomyces*, in particular *Saccharomyces carlsbergensis, Saccharomyces cerevisae, Saccharomyces kluyveri* and *Saccharomyces uvarum*, a strain of *Schizosaccharomyces* sp., in particular *Schizosaccharomyces pombe*, and a strain of *Yarrowia* sp., in particular *Yarrowia lipolytica*.

Examples of a host cell of plant origin which on cultivation may be capable of producing the enzyme of the invention is e.g. a plant cell of *Solanum tuberosum* or *Nicotiana tabacum*.

Method of Producing a Pectate Lyase Enzyme

In another aspect, the present invention also relates to a method of producing the enzyme preparation of the invention, the method comprising culturing a microorganism capable of producing the pectate lyase under conditions permitting the production of the enzyme, and recovering the enzyme from the culture. Culturing may be carried out using conventional fermentation techniques, e.g. culturing in shake flasks or fermentors with agitation to ensure sufficient aeration on a growth medium inducing production of the pectate lyase enzyme. The growth medium may contain a conventional N-source such as peptone, yeast extract or casamino acids, a reduced amount of a conventional C-source such as dextrose or sucrose, and an inducer such as pectinase or composite plant substrates such as cereal brans (e.g. wheat bran or rice husk). The recovery may be carried out using conventional techniques, e.g. separation of bio-mass and supernatant by centrifugation or filtration, recovery of the supernatant or disruption of cells if the enzyme of interest is intracellular, perhaps followed by further purification as described in EP 0 406 314 or by crystallization as described in WO 97/15660.

Further, the present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

As defined herein, an isolated polypeptide (e.g. an enzyme) is a polypeptide which is essentially free of other polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

The term "isolated polypeptide" may alternatively be termed "purified polypeptide".

When an expression vector comprising a DNA sequence encoding the enzyme is transformed into a heterologous host cell it is possible to enable heterologous recombinant production of the enzyme of the invention.

Thereby it is possible to make a highly purified or monocomponent pectate lyase composition, characterized in being free from homologous impurities.

In this context, homologous impurities mean any impurities (e.g. other polypeptides than the enzyme of the invention) which originate from the homologous cell where the enzyme of the invention is originally obtained from.

In the present invention the homologous host cell may be a strain of *Bacillus subtilis*.

The medium used to culture the transformed host cells may be any conventional medium suitable for growing the host cells in question. The expressed pectate lyase enzyme may conveniently be secreted into the culture medium and may be recovered there from by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

The present invention also relates to a transgenic plant, plant part or plant cell which has been transformed with a DNA sequence encoding the pectate lyase of the invention so as to express and produce this enzyme in recoverable quantities. The enzyme may be recovered from the plant or plant part.

The transgenic plant can be dicotyledonous or monocotyledonous, for short a dicot or a monocot. Examples of monocot plants are grasses, such as meadow grass (blue grass, *Poa*), forage grass such as *festuca, lolium*, temperate grass, such as *Agrostis*, and cereals, e.g. wheat, oats, rye, barley, rice, sorghum and maize (corn).

Examples of dicot plants are tobacco, legumes, such as lupins, potato, sugar beet, pea, bean and soybean, and cruciferous (family Brassicaceae), such as cauliflower, oil seed rape and the closely related model organism *Arabidopsis thaliana*.

Examples of plant parts are stem, callus, leaves, root, fruits, seeds, and tubers. In the present context, also specific plant tissues, such as chloroplast, apoplast, mitochondria, vacuole, peroxisomes and cytoplasm are considered to be a plant part. Furthermore, any plant cell, whatever the tissue origin, is considered to be a plant part.

Also included within the scope of the invention are the progeny of such plants, plant parts and plant cells.

The transgenic plant or plant cell expressing the enzyme of the invention may be constructed in accordance with methods known in the art. In short the plant or plant cell is constructed by incorporating one or more expression constructs encoding the enzyme of the invention into the plant host genome and propagating the resulting modified plant or plant cell into a transgenic plant or plant cell.

Conveniently, the expression construct is a DNA construct which comprises a gene encoding the enzyme of the invention in operable association with appropriate regulatory sequences required for expression of the gene in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, e.g. based on when, where and how the enzyme is desired to be expressed. For instance, the expression of the gene encoding the enzyme of the invention may be constitutive or inducible, or may be developmental, stage or tissue specific, and the gene product may be targeted to a specific tissue or plant part such as seeds or leaves. Regulatory sequences are e.g. described by Tague et al, Plant, Phys., 86, 506, 1988.

For constitutive expression the 35S-CaMV promoter may be used (Franck et al., 1980. Cell 21: 285-294). Organ-specific promoters may eg be a promoter from storage sink tissues such as seeds, potato tubers, and fruits (Edwards & Coruzzi, 1990. Annu. Rev. Genet. 24: 275-303), or from metabolic sink tissues such as meristems (Ito et al., 1994. Plant Mol. Biol. 24: 863-878), a seed specific promoter such as the glutelin, prolamin, globulin or albumin promoter from rice (Wu et al., Plant and Cell Physiology Vol. 39, No. 8 pp. 885-889 (1998)), a *Vicia faba* promoter from the legumin B4 and the unknown seed protein gene from *Vicia faba* described by Conrad U. et al, Journal of Plant Physiology Vol. 152, No. 6 pp. 708-711 (1998), a promoter from a seed oil body protein (Chen et al., Plant and cell physiology vol. 39, No. 9 pp. 935-941 (1998), the storage protein napA promoter from *Brassica napus*, or any other seed specific promoter known in the art, e.g. as described in WO 91/14772. Furthermore, the promoter may be a leaf specific promoter such as the rbcs promoter from rice or tomato (Kyozuka et al., Plant Physiology Vol. 102, No. 3 pp. 991-1000 (1993), the chlorella virus adenine methyltransferase gene promoter (Mitra, A. and Higgins, D W, Plant Molecular Biology Vol. 26, No. 1 pp. 85-93 (1994), or the aldP gene promoter from rice (Kagaya et al., Molecular and General Genetics Vol. 248, No. 6 pp. 668-674 (1995), or a wound inducible promoter such as the potato pin2 promoter (Xu et al, Plant Molecular Biology Vol. 22, No. 4 pp. 573-588 (1993).

A promoter enhancer element may be used to achieve higher expression of the enzyme in the plant. For instance, the promoter enhancer element may be an intron placed between the promoter and the nucleotide sequence encoding the enzyme. For instance, Xu et al. op cit disclose the use of the first intron of the rice actin 1 gene to enhance expression.

The selectable marker gene and any other parts of the expression construct may be chosen from those available in the art.

The DNA construct is incorporated into the plant genome according to conventional techniques known in the art, including *Agrobacterium*-mediated transformation, virus-mediated transformation, micro injection, particle bombardment, biolistic transformation, and electroporation (Gasser et al, Science, 244, 1293; Potrykus, Bio/Techn. 8, 535, 1990; Shimamoto et al, Nature, 338, 274, 1989).

Presently, *Agrobacterium tumefaciens* mediated gene transfer is the method of choice for generating transgenic dicots (for review Hooykas & Schilperoort, 1992. Plant Mol. Biol. 19: 15-38), however it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992. Plant J. 2: 275-281; Shimamoto, 1994. Curr. Opin. Biotechnol. 5: 158-162; Vasil et al., 1992. Bio/Technology 10: 667-674). An alternative method for transformation of monocots is based on protoplast transformation as described by Omirulleh S, et al., Plant Molecular biology Vol. 21, No. 3 pp. 415-428 (1993).

Following transformation, the transformants having incorporated the expression construct are selected and regenerated into whole plants according to methods well-known in the art.

Enzyme Compositions

In a still further aspect, the present invention relates to an enzyme composition comprising an enzyme exhibiting pectate lyase activity as described above.

The enzyme composition of the invention may, in addition to the pectate lyase of the invention, comprise one or more other enzyme types, for instance hemicellulase such as xylanase and mannanase, cellulase or endo-β-1,4-glucanase components, chitinase, lipase, esterase, pectinase, xyloglucanase, cutinase, phytase, oxidoreductase (peroxidase, haloperoxidase, oxidase, laccase), protease, amylase, reductase, phenoloxidase, ligninase, pullulanase, pectate lyase, pectin acetyl esterase, polygalacturonase, rhamnogalacturonase, pectin lyase, pectin methylesterase, cellobiohydrolase, transglutaminase; or mixtures thereof.

The enzyme composition may be prepared in accordance with methods known in the art and may be in the form of a liquid or a dry composition. For instance, the enzyme composition may be in the form of a granulate or a microgranulate. The enzyme to be included in the composition may be stabilized in accordance with methods known in the art.

Uses

Pectate lyases have potential uses in a lot of different industries and applications. However, the pectate lyase of the invention is especially useful as an ingredient of a detergent composition. Examples are given below of preferred uses of the enzyme composition of the invention. The dosage of the enzyme composition of the invention and other conditions under which the composition is used may be determined based on methods known in the art.

The pectate lyase of the present invention is an essential element of the detergent compositions of the present invention and is incorporated preferably at a level of from 0.0001% to 2%, more preferably from 0.0005% to 0.1%, most preferred from 0.001% to 0.02% pure enzyme by weight of the composition.

The pectate lyase of the invention, in addition to the enzyme core comprising the catalytically domain, may also contain a cellulose binding domain (CBD), the cellulose binding domain and enzyme core (the catalytically active domain) of the enzyme being operably linked. The cellulose-binding domain (CBD) may exist as an integral part of the encoded enzyme, or a CBD from another origin may be introduced into the enzyme thus creating an enzyme hybrid. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I-X), and demonstrates that CBDs are found in various enzymes such as cellulases, xylanases, mannanases, arabinofuranosidases, acetyl esterases and chitinases. CBDs have also been found in algae, e.g. the red alga *Porphyra purpurea* as a non-hydrolytic polysaccharide-binding protein, see Tomme et al., op.cit. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the pectate lyase enzyme and growing the host cell to express the fused gene. Enzyme hybrids may be described by the following formula:

CBD-MR-X wherein CBD is the N-terminal or the C-terminal region of an amino acid sequence corresponding to at least the cellulose binding domain; MR is the middle region (the linker), and may be a bond, or a short linking group preferably of from about 2 to about 100 carbon atoms, more preferably of from 2 to 40 carbon atoms; or is preferably from about 2 to about 100 amino acids, more preferably of from 2 to 40 amino acids; and X is an N-terminal or C-terminal region of the pectate lyase of the invention.

Use in the Detergent Industry

During washing and wearing, dyestuff from dyed fabrics or garment will conventionally bleed from the fabric, which then looks faded and worn. Removal of surface fibers from the fabric will partly restore the original colours and looks of the fabric. By the term "colour clarification", as used herein, is meant the partly restoration of the initial colours of fabric or garment throughout multiple washing cycles.

The term "de-pilling" denotes removing of pills from the fabric surface.

The term "soaking liquor" denotes aqueous liquor in which laundry may be immersed prior to being subjected to a conventional washing process. The soaking liquor may contain one or more ingredients conventionally used in a washing or laundering process.

The term "washing liquor" denotes aqueous liquor in which laundry is subjected to a washing process, i.e. usually a combined chemical and mechanical action either manually or in a washing machine. Conventionally, the washing liquor is an aqueous solution of a powder or liquid detergent composition.

The term "rinsing liquor" denotes aqueous liquor in which laundry is immersed and treated, conventionally immediately after being subjected to a washing process, in order to rinse the laundry, i.e. essentially remove the detergent solution from the laundry. The rinsing liquor may contain a fabric conditioning or softening composition.

The laundry subjected to the method of the present invention may be conventional washable laundry. Preferably, the major part of the laundry is sewn or unsown fabrics, including knits, wovens, denims, yarns, and towelling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, flax/linen, jute, cellulose acetate fibers, lyocell).

It has been surprisingly found that the detergent compositions the present invention do provide color clarification, de-pilling and clay stain removal, by the hydrolysing action of the pectate lyase on hemicellulose components from fabric fibers.

Removal of stains stemming from plants, wood, mould-clay based soils, muddy soils, and fruits is one of today's toughest cleaning task; especially with the trend toward low wash temperatures. These stains typically contain complex mixtures of fibrous material based mainly on carbohydrates and their derivatives: fibres and cell wall components. Food soils are often difficult to remove effectively from a soiled substrate. Highly coloured or "dried-on" soils derived from fruit and/or vegetable juices are particularly challenging to remove. Specific examples of such soils would include orange juice, tomato juice, banana, mango or broccoli soils. Indeed, pectin polymers are important constituents of plant cell walls. The substrates on which pectin containing stains are commonly found can be fabrics, dishware or hard surfaces.

It has been found that the detergent compositions of the present invention, including laundry, dishwashing and hard surface cleaning, provide superior cleaning and stain removal. Without whishing to be bound by theory, it is believed that the pectate lyase enzyme encompassed in the detergent composition of the present invention will very effectively hydrolyse pectins and pectates found in stains, thereby contributing to the stains removal. Indeed, as described above, such pectin and pectate components are found in the plant cell walls components of stains of vegetal and/or fruit origins, such as apple, bananas, tomatoes, orange, mango, avocados and grass stains. Pectin and pectate components are also extensively used in the food and beauty care industries, such as in ice creams, jams, shampoos and lipsticks.

Furthermore, it has been found that the detergent compositions of the present invention when formulated as a laundry composition, will provide fabric softness. Without whishing to be bound by theory, it is believed that the pectins and pectate components found on the fabric stains, by their acidic nature, bind strongly calcium and cationic atoms, rendering the fabric harsh. It is believed that the removal of those pectins and pectate components will prevent the binding of those calcium and cationic atoms and hence, provide some softening effects.

DETERGENT DISCLOSURE AND EXAMPLES

Surfactant System

The detergent compositions according to the present invention comprise a surfactant system, wherein the surfactant can be selected from non-ionic and/or anionic and/or cationic and/or ampholytic and/or zwitterionic and/or semi-polar surfactants.

The surfactant is typically present at a level from 0.1% to 60% by weight.

The surfactant is preferably formulated to be compatible with enzyme components present in the composition. In liquid or gel compositions the surfactant is most preferably formulated in such a way that it promotes, or at least does not degrade, the stability of any enzyme in these compositions.

Preferred systems to be used according to the present invention comprise as a surfactant one or more of the non-ionic and/or anionic surfactants described herein. More preferably, the compositions of the present invention will comprise a high level of anionic surfactants, i.e. up to 30%, preferably from 10-25% by weight expressed in free acid. Preferred anionic surfactants to be used therein are alkylbenzene sulfonate in the acid form, alkyl sulfates and alkyl ethoxy sulfates, as described below. In a further preferred embodiment, the high anionic surfactant compositions of the present invention will further comprise amine oxide surfactant and/or an amido amines such as amidopropyl diethylamine. It has been found that the detergent compositions of the present invention, including laundry, dishwashing and hard surface cleaning, further comprising a high level of anionic surfactants, will provide excellent cleaning and stain removal. Without wishing to be bound by theory, it is believed that the anionic surfactant will help solubilising the small pectin fragments hydrolysed by the enzyme of the invention and prevent them from redepositing on the surface to be cleaned.

Suitable anionic surfactants to be used are alkyl ester sulfonate surfactants including linear esters of $C_8$-$C_{20}$ carboxylic acids (i.e., fatty acids), which are, sulfonated with gaseous $SO_3$ according to "The Journal of the American Oil Chemists Society", 52 (1975), pp. 323-329. Suitable starting materials would include natural fatty substances as derived from tallow, pahn oil, etc.

The preferred alkyl ester sulfonate surfactant, especially for laundry applications, comprise alkyl ester sulfonate surfactants of the structural formula:

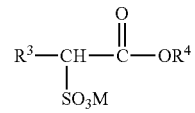

wherein $R^3$ is a $C_8$-$C_{20}$ hydrocarbyl, preferably an alkyl, or combination thereof, $R^4$ is a $C_1$-$C_6$ hydrocarbyl, preferably an alkyl, or combination thereof, and M is a cation, which forms a water-soluble salt with the alkyl ester sulfonate. Suitable salt-forming cations include metals such as sodium, potassium, and lithium, and substituted or unsubstituted ammonium cations, such as monoethanolamine, diethanolamine, and triethanolamine. Preferably, $R^3$ is $C_{10}$-$C_{16}$ alkyl, and $R^4$ is methyl, ethyl or isopropyl. Especially preferred are the methyl ester sulfonates wherein $R^3$ is $C_{10}$-$C_{16}$ alkyl.

Other suitable anionic surfactants include the alkyl sulfate surfactants which are water soluble salts or acids of the formula $ROSO_3M$ wherein R preferably is a $C_{10}$-$C_{24}$ hydrocarbyl, preferably an alkyl or hydroxyalkyl having a $C_{10}$-$C_{20}$ alkyl component, more preferably a $C_{12}$-$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethylammonium and dimethyl piperdinium cations and quaternary ammonium cations derived from alkylamines such as ethylamine, diethylamine, triethylamine, and mixtures thereof, and the like). Typically, alkyl chains of $C_{12}$-$C_{16}$ are preferred for lower wash temperatures (e.g. below about 50° C.) and $C_{16}$-$C_{18}$ alkyl chains are preferred for higher wash temperatures (e.g. above about 50° C.).

Other anionic surfactants useful for detersive purposes can also be included in the laundry detergent compositions of the present invention. Theses can include salts (including, for example, sodium, potassium, ammonium, and substituted ammonium salts such as mono- di- and triethanolamine salts) of soap, $C_8$-$C_{22}$ primary or secondary alkanesulfonates, $C_8$-$C_{24}$ olefinsulfonates, sulfonated polycarboxylic acids prepared by sulfonation of the pyrolyzed product of alkaline earth metal citrates, e.g., as described in British patent specification No. 1,082,179, $C_8$-$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$-$C_{18}$ monoesters) and diesters of sulfosuccinates (especially saturated and unsaturated $C_6$-$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)_k$—$CH_2COO$-M+ wherein R is a $C_8$-$C_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vol. I and II by Schwartz, Perry and Berch). A variety of such surfactants are also generally disclosed in U.S. Pat. No. 3,929,678, (Column 23, line 58 through Column 29, line 23, herein incorporated by reference).

Further preferred anionic surfactants include alkyl alkoxylated sulfate surfactants. Examples hereof are water soluble salts or acids of the formula $RO(A)_m SO3M$ wherein R is an unsubstituted $C_{10}$-$C_{24}$ alkyl or hydroxyalkyl group having a $C_{10}$-$C_{24}$ alkyl component, preferably a $C_{12}$-$C_{20}$ alkyl or hydro-xyalkyl, more preferably $C_{12}$-$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethyl amine, triethylamine, mixtures thereof, and the like. Exemplary surfactants are $C_{12}$-$C_{18}$ alkyl polyethoxylate (1.0) sulfate ($C_{12}$-$C_{18}E(1.0)M$), $C_{12}$-$C_{18}$ alkyl polyethoxylate (2.25) sulfate ($C_{12}$-$C_{18}(2.25)$M, and $C_{12}$-$C_{18}$ alkyl polyethoxylate (3.0) sulfate ($C_{12}$-$C_{18}E(3.0)M$), and $C_{12}$-$C_{18}$ alkyl polyethoxylate (4.0) sulfate ($C_{12}$-$C_{18}E(4.0)M$), wherein M is conveniently selected from sodium and potassium. When included therein, the laundry detergent compositions of the present invention typically comprise from about 1% to about 40%, preferably from about 3% to about 20% by weight of such anionic surfactants.

Polyethylene, polypropylene, and polybutylene oxide conden-sates of alkyl phenols are suitable for use as the non-ionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available non-ionic surfactants of this type include Igepal™ CO-630, marketed by the GAF Corporation; and Triton™ X-45, X-114, X-100 and X-102, all marketed by the Rohm & Haas Company. These surfactants are commonly referred to as alkyl phenol alkoxylates (e.g., alkyl phenol ethoxylates).

The condensation products of primary and secondary aliphatic alcohols with about 1 to about 25 moles of ethylene oxide are suitable for use as the non-ionic surfactant of the non-ionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available non-ionic surfactants of this type include Tergitol™ 15-S-9 (The condensation product of $C_{11}$-$C_{15}$ linear alcohol with 9 moles ethylene oxide), Tergitol™ 24-L-6 NMW (the condensation product of $C_{12}$-$C_{14}$ primary alcohol with 6 moles ethylene oxide with a narrow molecular weight distribution), both marketed by Union Carbide Corporation; Neodol™ 45-9 (the condensation product of $C_{14}$-$C_{15}$ linear alcohol with 9 moles of ethylene oxide), Neodol™ 23-3 (the condensation product of $C_{12}$-$C_{13}$ linear alcohol with 3.0 moles of ethylene oxide), Neodol™ 45-7 (the condensation product of $C_{14}$-$C_{15}$ linear alcohol with 7 moles of ethylene oxide), Neodol™ 45-5 (the condensation product of $C_{14}$-$C_{15}$ linear alcohol with 5 moles of ethylene oxide) marketed by Shell Chemical Company, Kyro™ EOB (the condensation product of $C_{13}$-$C_{15}$ alcohol with 9 moles ethylene oxide), marketed by The Procter & Gamble Company, and Genapol LA 050 (the condensation product of $C_{12}$-$C_{14}$ alcohol with 5 moles of ethylene oxide) marketed by Hoechst. Preferred range of HLB in these products is from 8-11 and most preferred from 8-10.

Also useful as the non-ionic surfactant of the surfactant systems of the present invention are alkyl polysaccharides disclosed in U.S. Pat. No. 4,565,647, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

The preferred alkyl polyglycosides have the formula:

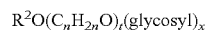

wherein $R^2$ is selected from the group consisting of alkyl, alkyl phenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional non-ionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the non-ionic surfactant of the non-ionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of non-ionic surfactant include certain of the commercially available Tetronic™ compounds, marketed by BASF.

Preferred for use as the non-ionic surfactant of the surfactant systems of the present invention are polyethylene oxide condensates of alkyl phenols, condensation products of primary and secondary aliphatic alcohols with from about 1 to about 25 moles of ethylene oxide, alkyl polysaccharides, and mixtures hereof Most preferred are $C_8$-$C_{14}$ alkyl phenol ethoxylates having from 3 to 15 ethoxy groups and $C_8$-$C_{18}$ alcohol ethoxylates (preferably $C_{10}$ avg.) having from 2 to 10 ethoxy groups, and mixtures thereof.

Highly preferred non-ionic surfactants are polyhydroxy fatty acid amide surfactants of the formula

wherein $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxy hydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$ alkyl or alkenyl chain such as coconut alkyl or mixtures thereof, and Z is derived from a reducing sugar such as glucose, fructose, maltose or lactose, in a reductive amination reaction.

The laundry detergent compositions of the present invention may also contain cationic, ampholytic, zwitterionic, semi-polar surfactants and/or cosurfactants, as well as the nonionic and/or anionic surfactants other than those already described herein. When included therein, the detergent compositions of the present invention typically comprise from 0.2% to about 25%, preferably from about 1% to about 8% by weight of such cationic surfactants, ampholytic, zwitterionic, and/or semi-polar surfactants.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

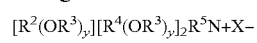

wherein $R^2$ is an alkyl or alkyl benzyl group having from about 8 to about 18 carbon atoms in the alkyl chain, each $R^3$ is selected form the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$-$C_4$ alkyl, $C_1$-$C_4$ hydroxyalkyl, benzyl ring structures formed by joining the two $R^4$ groups, —$CH_2CHOHCHOHCOR^6CHOHCH_2OH$, wherein $R^6$ is any hexose or hexose polymer having a molecular weight less than about 1000, and hydrogen when y is not 0; $R^5$ is the same as $R^4$ or is an alkyl chain, wherein the total number of carbon atoms or $R^2$ plus $R^5$ is not more than about 18; each y is from 0 to about 10, and the sum of the y values is from 0 to about 15; and X is any compatible anion.

Highly preferred cationic surfactants are the water soluble quaternary ammonium compounds useful in the present composition having the formula: $R_1R_2R_3R_4N^+X^-$ (i) wherein $R_1$ is $C_8$-$C_{16}$ alkyl, each of $R_2$, $R_3$ and $R_4$ is independently $C_1$-$C_4$ alkyl, $C_1$-$C_4$ hydroxy alkyl, benzyl, and —$(C_2H_{4O})_xH$ where x has a value from 2 to 5, and X is an anion. Not more than one of $R_2$, $R_3$ or $R_4$ should be benzyl.

The preferred alkyl chain length for $R_1$ is $C_{12}$-$C_{15}$, particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:
 coconut trimethyl ammonium chloride or bromide;
 coconut methyl dihydroxyethyl ammonium chloride or bromide;
 decyl triethyl ammonium chloride;
 decyl dimethyl hydroxyethyl ammonium chloride or bromide;
 $C_{12-15}$ dimethyl hydroxyethyl ammonium chloride or bromide;
 coconut dimethyl hydroxyethyl ammonium chloride or bromide;
 myristyl trimethyl ammonium methyl sulphate;
 lauryl dimethyl benzyl ammonium chloride or bromide;
 lauryl dimethyl (ethenoxy)$_4$ ammonium chloride or bromide;
 choline esters (compounds of formula (i) wherein $R_1$ is

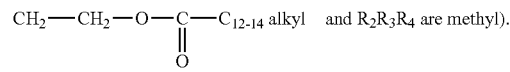

di-alkyl imidazolines [compounds of formula (i)].

Other cationic surfactants useful herein are also described in U.S. Pat. No. 4,228,044 and in EP 000 224.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 (column 19, lines 18-35) for examples of ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

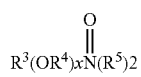

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$-$C_{18}$ alkyl dimethyl amine oxides and $C_8$-$C_{12}$ alkoxy ethyl dihydroxy ethyl amine oxides.

Suitable co-surfactants are selected from the group of primary or tertiary amines.

Suitable primary amines for use herein include amines according to the formula $R_1NH_2$ wherein $R_1$ is a $C_6$-$C_{12}$, preferably $C_6$-$C_{10}$ alkyl chain or $R_4X(CH_2)_n$, X is —O—, —C(O)NH— or —NH—, $R_4$ is a $C_6$-$C_{12}$ alkyl chain n is between 1 to 5, preferably 3. $R_1$ alkyl chains may be straight or branched and may be interrupted with up to 12, preferably less than 5 ethylene oxide moieties.

Preferred amines according to the formula herein above are n-alkyl amines. Suitable amines for use herein may be selected from 1-hexylamine, 1-octylamine, 1-decylamine and laurylamine. Other preferred primary amines include C8-C10 oxypropylamine, octyloxypropylamine, 2-ethylhexyl-oxypropylamine, lauryl amido propylamine and amido propylamine.

Suitable tertiary amines for use herein include tertiary amines having the formula $R_1R_2R_3N$ wherein R1 and R2 are $C_1$-$C_8$ alkyl chains or

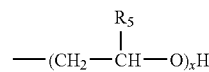

$R_3$ is either a $C_6$-$C_{12}$, preferably $C_6$-$C_{10}$ alkyl chain, or $R_3$ is $R_4X(CH_2)_n$, whereby X is —O—, —C(O)NH— or —NH—, $R_4$ is a $C_4$-$C_{12}$, n is between 1 to 5, preferably 2-3. $R_5$ is H or $C_1$-$C_2$ alkyl and x is between 1 to 6.

$R_3$ and $R_4$ may be linear or branched; $R_3$ alkyl chains may be interrupted with up to 12, preferably less than 5, ethylene oxide moieties. Preferred tertiary amines are $R_1R_2R_3N$ where R1 is a C6-C12 alkyl chain, R2 and R3 are C1-C3 alkyl or

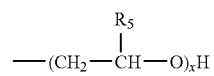

where R5 is H or CH3 and x=1-2.

Also preferred are the amidoamines of the formula:

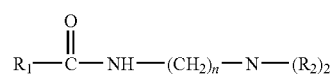

wherein $R_1$ is $C_6$-$C_{12}$ alkyl; n is 2-4, preferably n is 3; $R_2$ and $R_3$ is $C_1$-$C_4$ Most preferred amines include 1-octylamine, 1-hexylamine, 1-decylamine, 1-dodecylamine, C8-10oxypropylamine, N coco 1-3diaminopropane, coconutalkyldinethylamine, lauryldimethylamine, lauryl bis(hydroxyethyl) amine, coco bis(hydroxyehtyl)amine, lauryl amine 2 moles propoxylated, octyl amine 2 moles propoxylated, lauryl amidopropyldimethylamine, C8-10 amidopropyldimethylamine and C10 amidopropyl-dimethylamine.

The most preferred amines for use in the compositions herein are 1-hexylamine, 1-octylamine, 1-decylamine, 1-dodecylamine. Especially desirable are n-dodecyldimethylamine and bishydroxyethylcoconutalkylamine and oleylamine 7 times ethoxylated, lauryl amido propylamine and cocoamido propylamine.

Builder System

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenle-enschrift 2,446,686, and 2,446,487, U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2,-ethane tetracarboxylates, 1,1,3,3-propane tetrac7arboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadienide pentacarboxylates, 2,3,4,5-tetrahydro-furan-cis,cis,cis-tetracarboxylates, 2,5-tetrahydro-furan-cis, discarboxylates, 2,2,5,5,-tetrahydrofuran-tetracarboxylates, 1,2,3,4,5,6-hexane-hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent composiions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MGEDDS and $Mg_2EDDS$. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in GB-A-1,596,756. Examples of such salts are polyacrylates of MW 2000-5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

Preferred detergent compositions, in addition to the enzyme preparation of the invention, comprise other enzyme(s) which provides cleaning performance and/or fabric care benefits.

Such enzymes include proteases, lipases, cutinases, amylases, cellulases, peroxidases, oxidases (e.g. laccases)

Proteases: Any protease suitable for use in alkaline solutions can be used. Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270.

Preferred commercially available protease enzymes include those sold under the trade names Alcalase, Savinase, Primase, Durazym, and Esperase by Novozymes A/S (Denmark), those sold under the tradename Maxatase, Maxacal, Maxapem, Properase, Purafect and Purafect OXP by Genencor International, and those sold under the tradename Opticlean and Optimase by Solvay Enzymes. Protease enzymes may be incorporated into the compositions in accordance with the invention at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Lipases: Any lipase suitable for use in alkaline solutions can be used. Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a *Candida* lipase, such as a *C. antarctica* lipase, e.g., the *C. antarctica* lipase A or B described in EP 214 761, a *Pseudomonas lipase* such as a *P. alcaligenes* and *P. pseudoalcaligenes* lipase, e.g., as described in EP 218 272, a *P. cepacia* lipase, e.g., as described in EP 331 376, a *P. stutzeri* lipase, e.g., as disclosed in GB 1,372,034, a *P. fluorescens* lipase, a *Bacillus lipase*, e.g., a *B. subtilis* lipase (Dartois et al., (1993), Biochemica et Biophysica acta 1131, 253-260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61-67), the *Geotricum candidum* lipase (Schimada, Y. et al., (1989), J. Biochem., 106, 383-388), and various *Rhizopus* lipases such as a *R. delemar* lipase (Hass, M. J et al., (1991), Gene 109, 117-113), a *R. niveus* lipase (Kugimiya et al., (1992), Biosci. Biotech. Biochem. 56, 716-719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani pisi* (e.g. described in WO 90/09446).

Especially suitable lipases are lipases such as M1 Lipase™, Luma fast™ and Lipomax™ (Genencor), Lipolase™ and Lipolase Ultra™ (Novozymes A/S), and Lipase P "Amano" (Amano Pharmaceutical Co. Ltd.).

The lipases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Amylases: Any amylase (a and/or b) suitable for use in alkaline solutions can be used. Suitable amylases include those of bacterial or fungal origin. Chemically or genetically modified mutants are included. Amylases include, for example, a-amylases obtained from a special strain of *B. licheniformis*, described in more detail in GB 1,296,839. Commercially available amylases are Duramyl™, Termamyl™, Fungamyl™ and BAN™ (available from Novozymes A/S) and Rapidase™ and Maxamyl P™ (available from Genencor).

The amylases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Cellulases: Any cellulase suitable for use in alkaline solutions can be used. Suitable cellulases include those of bacterial or fungal origin. Chemically or genetically modified mutants are included. Suitable cellulases are disclosed in U.S. Pat. No. 4,435,307 and WO 91/17243 which disclose fungal cellulases produced from *Humicola insolens*, in WO 96/34108 and WO 96/34092 which disclose bacterial alkalophilic cellulases (BCE 103) from *Bacillus*, and in WO 94/21801, U.S. Pat. Nos. 5,475,101 and 5,419,778 which disclose EG III cellulases from *Trichoderma*. Especially suitable cellulases are the cellulases having colour care benefits. Examples of such cellulases are cellulases described in European patent application No. 0 495 257. Commercially available cellulases include Celluzyme™and Carezyme™ produced by a strain of *Huinicola insolens* (Novozymes A/S), KAC-500(B)™ (Kao Corporation), and Puradax™ (Genencor International).

Cellulases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Peroxidases/Oxidases: Peroxidase enzymes are used in combination with hydrogen peroxide or a source thereof (e.g. a percarbonate, perborate or persulfate). Oxidase enzymes are used in combination with oxygen. Both types of enzymes are used for "solution bleaching", i.e. to prevent transfer of a textile dye from a dyed fabric to another fabric when said fabrics are washed together in a wash liquor, preferably together with an enhancing agent as described in e.g. WO 94/12621 and WO 95/01426. Suitable peroxidases/oxidases include those of plant, bacterial or fungal origin. Chemically or genetically modified mutants are included.

Peroxidase and/or oxidase enzymes are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Mixtures of the above mentioned enzymes are encompassed herein, in particular a mixture of a protease, an amylase, a lipase and/or a cellulase.

The enzyme of the invention, or any other enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Bleaching Agents

Additional optional detergent ingredients that can be included in the detergent compositions of the present invention include bleaching agents. These bleaching agent components can include one or more oxygen bleaching agents and, depending upon the bleaching agent chosen, one or more bleach activators. When present oxygen bleaching compounds will typically be present at levels of from about 1% to about 25%. Preferred bleaching agents for the compositions of the present inventions are the Transition Metal Complexes of Macropolycyclic Rigid Ligand as described below, especially the Dichloro Mn dimethyl ethylene-bridged Cyclam and/or Dichloro Mn diethyl ethylene-bridged Cyclam; and the combination of an hydrogen peroxide releasing agents with the bleach activator 4-[N-(nonaoyl) amino hexanoyloxy]-benzene sulfonate sodium salt (NACA-OBS).

It has been found that the detergent compositions of the present invention, including laundry, dishwashing and hard surface cleaning, further comprising a bleaching agent, will provide excellent cleaning and stain removal. Without wishing to be bound by theory, it is believed that the bleaching agent will further oxidise the hydroxyl groups in the pectin/ pectate components, redering them more soluble and easier to remove.

It has been surprisingly found that bleach systems can maximise the pectate lyase enzyme cleaning efficiency. Further it has been surprisingly found that detergent compositions comprising the pectate lyase of the invention and a bleach system, provide superior cleaning due to the synergistic effect of the bleach system providing cleaning, stain removal and in a laundry context whiteness maintenance, and the pectate lyase degrading the pectin components of such soil and/or, in a laundry context, the pectin component of the fabrics that can bind such soils. These bleach systems—enzyme mixed systems deliver an outstanding cleaning effect, especially on food coloured stains and body soils. Moreover, when formulated as a laundry and/or fabric care composition, the compositions of the present invention provide synergistic whiteness maintenance.

Without wishing to be bound by theory, it is believed that the natural pectins found in many common fruit and vegetable based soils as well as the primary wall of cotton fibers attract and hold soil residues, particularly highly colored soil components. Removal of the pectin component with pectate lyase exposes these color bodies to the bleach system. It is believed that the synergistic effect is due to these bleach systems decolourizing the colour components of tough to remove food stains and body soils and the pectate lyase degrading the pectin components of such soil and/or in a laundry context, the pectin components of the fabrics that can bind or otherwise interact with such soils, making said soils difficult to remove.

The bleaching agent component for use herein can be any of the bleaching agents useful for detergent compositions including oxygen bleaches as well as others known in the art: such as monohydrated or tetrahydrated perborate and percarbonate with a particle size of 400-800 microns.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching is agents are disclosed in U.S. Pat. Nos. 4,483,781, 740,446, EP 0 133 354 and U.S. Pat. No. 4,412,934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5-10% by weight of the finished product, preferably 1-5% by weight.

The hydrogen peroxide releasing agents can be used in combination with bleach activators such as tetra-acetylethylenediamine (TAED), nonanoyloxybenzenesulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamido-caproyl)oxybenzenesulfonate, C9(6-nonanamido caproyl) oxybenzenesulfonate and C10 (6-decanamido caproyl)oxybenzenesulfonate or mixtures thereof. Further hydrophobic bleach activators include, but are not limited to, 4-[N-(nonaoyl) amino hexanoyloxy]-benzene sulfonate sodium salt (NACA-OBS) an example of which is described in U.S. Pat. No. 5,523,434, dodecanoyloxybenzenesulphonate (LOBS or $C_{12}$-OBS), 10-undecenoyloxybenzenesulfonate (UDOBS or $C_{11}$-OBS with unsaturation in the 10 position), and decanoyloxybenzoic acid (DOBA). Also suitable activators are acylated citrate esters such as disclosed in EP 624 154.

Useful bleaching agents, including peroxyacids and bleaching systems comprising bleach activators and peroxygen bleaching compounds for use in detergent compositions according to the invention are described in WO95/10592.

The hydrogen peroxide may also be present by adding an enzymatic system (i.e. an enzyme and a substrate therefore) which is capable of generation of hydrogen peroxide at the beginning or during the washing and/or rinsing process. Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc and/or aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine. Bleaching agents may also comprise a manganese and cobalt catalysts as described in for example, the manganese-based catalysts disclosed in U.S. Pat. Nos. 5,576,282; 5,246,621; 5,244,594; 5,194,416; and 5,114,606; and European Pat. App. Pub. Nos. 549,271 A1, 549,272 A1, 544,440 A2, and 544,490 A1; for example, the cobalt bleach catalysts are described, for example, in U.S. Pat. Nos. 5,597,936; 5,595,967; and 5,703,030; and M. L. To be, "Base Hydrolysis of Transition-Metal Complexes", *Adv. Inorg. Bioinorg. Mech.,* (1983), 2, pages 1-94.

Compositions herein may also suitably include as bleach catalyst a transition metal complex of a macropolycyclic rigid ligand. The amount used is a catalytically effective amount, suitably about 1 ppb or more, for example up to about 99.9%, more typically about 0.001 ppm or more, preferably from about 0.05 ppm to about 500 ppm Transition-metal bleach catalysts of Macrocyclic Rigid Ligands which are suitable for use in the invention compositions are non-limitingly illustrated by any of the following:

Dichloro-5,12-dimethyl-1,5,8,12-tetraazabicyclo[6.6.2]hexadecane Manganese(II)

Dichloro-4,11-dimethyl-1,4,8,11-tetraazabicylco[6.6.2]hexadecane Manganese(II)

Dichloro-5,12-diethyl-1,5,8,12-tetraazabicyclo[6.6.2]hexadecane Manganese(II)

Dichloro-4,11-diethyl-1,4,8,11-tetraazabicylco[6.6.2]hexadecane Manganese(II)

Diaquo-5,12-dimethyl-1,5,8,12-tetraazabicyclo[6.6.2]hexadecaneManganese(II)-Hexafluorophosphate Aquo-hydroxy-5,12-dimethyl-1,5,8,12-etraazabicyclo[6.6.2]hexadecaneManganese(III)-Hexafluorophosphate Diaquo-5,12-dimethyl-1,5,8,12-tetraazabicyclo[6.6.2]hexadecaneManganese(II)-Tetrafluoroborate Dichloro-5,12-dimethyl-1,5,8,12-tetraazabicyclo[6.6.2]hexadecaneManganese(III)-Hexafluorophosphate Dichloro-5,12-di-n-butyl-1,5,8,12-tetraazabicyclo[6.6.2]hexadecaneManganese(II)

Dichloro-5,12-dibenzyl-1,5,8,12-tetraazabicyclo[6.6.2]hexadecaneManganese(II) Dichloro-5-n-butyl-12-methyl-1,5,8,12-tetraaza-bicyclo[6.6.2]hexadecaneManganese(II)

Dichloro-5-n-octyl-12-methyl-1,5,8,12-tetraaza-bicyclo[6.6.2]hexadecaneManganese(II)

Dichloro-5-n-butyl-12-methyl-1,5,8,12-tetraaza-bicyclo [6.6.2]hexadecaneManganese(II).

Suds Suppressors

Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or water dispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available form Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofol 12 R.

Such suds suppressor system are described in European Patent Application EP 0 593 841.

Especially preferred silicone suds controlling agents are described in European Patent Application No. 92201649.8. Said compositions can comprise a silicone/silica mixture in combination with fumed nonporous silica such as Aerosil®.

The suds suppressors described above are normally employed at levels of from 0.001% to 2% by weight of the composition, preferably from 0.01% to 1% by weight.

Other Components

Other components used in detergent compositions may be employed such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water soluble capsules which consist of a matrix of polysaccharide and polyhydroxy compounds such as described in GB 1,464, 616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2' disulphonate, disodium 4-4'-bis-(2-morpholino-4-anilino-s-triazin-6-ylamino-stilbene-2:2'-disulphonate, disodium 4,4'-bis-(2,4-dianilino-s-triazin-6-ylamino)stilbene-2:2'-disulphonate, monosodium 4',4"-bis-(2,4-dianilino-s-tri-azin-6 ylamino) stilbene-2-sulphonate, disodium 4,4'-bis-(2-anilino-4-(N-methyl-N-2-hydroxyethylamino)-s-triazin-6-ylamino)stilbene-2,2'-disulphonate, di-sodium 4,4'-bis-(4-phenyl-2,1,3-triazol-2-yl)-stilbene-2,2' disulphonate, di-so-dium 4,4'bis(2-anilino-4-(1-methyl-2-hydroxyethylamino)-s-triazin-6-ylami-no)stilbene-2,2'disulphonate, sodium 2(stilbyl-4"-(naphtho-1',2':4,5)-1,2,3-triazole-2"-sulphonate and 4,4'-bis (2-sulphostyryl)biphenyl.

Other useful polymeric materials are the polyethylene glycols, particularly those of molecular weight 1000-10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. Nos. 4,116,885 and 4,711,730 and EP 0 272 033. A particular preferred polymer in accordance with EP 0 272 033 has the formula:

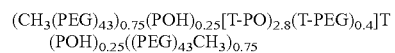

where PEG is —(OC$_2$H$_4$)0-, PO is (OC$_3$H$_6$O) and T is (pOOC$_6$H$_4$CO).

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311 342.

Softening Agents

Fabric softening agents can also be incorporated into laundry detergent compositions in accordance with the present invention. These agents may be inorganic or organic in type. Inorganic softening agents are exemplified by the smectite clays disclosed in GB-A-1 400898 and in U.S. Pat. No. 5,019, 292. Organic fabric softening agents include the water insoluble tertiary amines as disclosed in GB-A1 514 276 and EP 0 011 340 and their combination with mono $C_{12}$-$C_{14}$ quaternary ammonium salts are disclosed in EP-B-0 026 528 and di-long-chain amides as disclosed in EP 0 242 919. Other useful organic ingredients of fabric softening systems include high molecular weight polyethylene oxide materials as disclosed in EP 0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric Dye-transfer Inhibiting Agents

The detergent compositions according to the present invention may also comprise from 0.001% to 10%, preferably from 0.01% to 2%, more preferably form 0.05% to 1% by weight of polymeric dye-transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinyl-pyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

The detergent composition according to the invention can be in liquid, paste, gels, bars or granular forms.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e. they may have a relatively higher density than conventional granular detergents, i.e. form 550 to 950 g/l; in such case, the granular detergent compositions according to the present invention will contain a lower amount of "Inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions according to the present invention can also be in "concentrated form", in such case, the liquid detergent compositions according to the present invention will contain a lower amount of water, compared to conventional liquid detergents. Typically, the water content of the concentrated liquid detergent is less than 30%, more preferably less than 20%, most preferably less than 10% by weight of the detergent compositions.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The following examples are meant to exemplify compositions for the present invention, but are not necessarily meant to limit or otherwise define the scope of the invention. In the detergent compositions, the abbreviated component identifications have the following meanings:

LAS: Sodium linear $C_{12}$ alkyl benzene sulphonate
TAS: Sodium tallow alkyl sulphate
XYAS: Sodium $C_{1X}$-$C_{1Y}$ alkyl sulfate
ABEY: A $C_{1A}$-$C_{1B}$ predominantly linear primary alcohol condensed with an average of Y moles of ethylene oxide
XYEZS: $C_{1X}$-$C_{1Y}$ sodium alkyl sulfate condensed with an average of Z moles of ethylene oxide per mole
Nonionic: $C_{13}$-$C_{15}$ mixed ethoxylatedlpropoxylated fatty alcohol with an average degree of ethoxylation of 3.8 and an average degree of propoxylation of 4.5 sold under the tradename Plurafax LF404 by BASF GmbH
CFAA: $C_{12}$-$C_{14}$ alkyl N-methyl glucamide
TFAA: $C_{16}$-$C_{18}$ alkyl N-methyl glucamide
QAS: $R_2.N+(CH_3)_2(C_2H_4OH)$ with $R_2=C_{12}$-$C_{14}$
DTPA: Diethylene triamine pentaacetic acid
SADS: Sodium $C_{14-22}$ alkyl disulfate of the formula 2-R.$C_4H_7$.-1,4-($SO_4$—)2 where R=$C_{10-18}$
MES: x-sulpho methyl ester of $C_{18}$ fatty acid
Soap: Sodium linear alkyl carboxylate derived from a 80/20 mixture of tallow and coconut fatty acids
Silicate: Amorphous Sodium Silicate (SiO2:$Na_2O$ ratio=2.0)
NaSKS-6: Crystalline layered silicate of formula d-$Na_2Si_2O_5$
Carbonate: Anhydrous sodium carbonate
MA/AA: Copolymer of 1:4 maleic/acrylic acid, average molecular weight about 80,000
Zeolite A: Hydrated Sodium Aluminosilicate of formula $Na_{12}(AlO_2SiO_2)_{12}.27H_2O$ having a primary particle size in the range from 1 to 10 micrometers
Citrate: Tri-sodium citrate dihydrate
PB1: Anhydrous sodium perborate monohydrate bleach
Percarbonate: Anhydrous sodium percarbonate bleach of empirical formula $2Na_2CO_3.3H_2O_2$
TAED: Tetraacetyl ethylene diamine
NACA-OBS: 4-[N-(nonaoyl)amino hexanoyloxy]-benzene sulfonate sodium salt
NOBS: Nonanoyloxybenzene sulfonate in the form of the sodium salt
CMC: Sodium carboxymethyl cellulose
HEDP: Hydroxyethane dimethylene phosphonic acid
DETPMP: Diethylene triamine penta (methylene phosphonic acid), marketed by Monsanto under the Tradename Dequest 2060
TEPAE: Tetreaethylenepentaamine ethoxylate
PVP: Polyvinylpyrrolidone polymer
PVPVI: Poly (4-vinylpyridine)-N-Oxide/copolymer of vinyl-imidazole and vinyl-pyrrolidone PVNO Polyvinylpyridine-N-Oxide, with an average molecular weight of 50,000

Brightener: Disodium 4,4'-bis(2-sulphostyryl)biphenyl and/or Disodium 4,4'-bis(4-anilino-6-morpholino-1.3.5-triazin-2-yl) stilbene-2:2'-disulfonate EDDS: Ethylenediamine-N,N-disuccinic acid, [S,S] isomer in the form of the sodium salt Suds Suppressor: 25% paraffin wax Mpt 50° C., 17% hydrophobic silica, 58% paraffin oil Granular Suds suppressors: 12% Silicone/silica, 18% stearyl alcohol, 70% starch in granular form Sulphate: Anhydrous sodium sulphate HMWPEO: High molecular weight polyethylene oxide Enzymes: Protease, amylase, cellulase, lipase as described above in the description Metal catalyst: Dichloro Mn diethyl ethylene-bridged Cyclam Amine: C8-10 amidopropyldiethylamine SRP: Anionically end capped poly esters STPP: Sodium tripolyphosphate Bicarbonate: Sodium hydrogen carbonate PAAC: Pentaamine acetate cobalt (III) salt Paraffin: Paraffin oil sold under the tradename Winog 70 by Wintershall.

BTA: Benzotriazole

Triacetate Sodium acetate trihydrate

PEG X: Polyethylene Glycol molecular weight approximately X

SKTP: Sodium potassium tripolyphosphate

SLF18: low foaming surfactant available from Olin Corporation

ACNI: alkyl capped non-ionic surfactant of formula $C_{9/11}H_{19/23}$ $EO_8$-cyclohexyl acetal PA30: Polyacrylate homo-polymer of molecular weight approximately 8,000 available from BASF Polygel premix: 5% active Polygel DKP in water available from 3V Inc.

BTA: Benzotriazole

MEA: Monoethanolamine

The enzyme component(s) are encompassed within those examples in % pure enzyme by weight of total composition.

The following non-limiting examples illustrate the invention.

Materials and Methods

Strains and Donor Organism

*Bacillus subtilis* DSM 14218 comprises the plasmid containing the DNA encoding the pectate lyase of the invention (SEQ ID NO:1). The gene can also be cloned from strain ATCC 23857 (*B. subtilis* PL2306) or the DNA from the same strain ATCC 23857D (both obtainable from ATCC, LGC Promochem AB, PO Box 1737, SE-501 17 Boras, Sweden).

*B. subtilis* PL1801. This strain is the *B. subtilis* DN1885 with disrupted apr and npr genes (Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol., 172, 4315-4321) disrupted in the transcriptional unit of the klnown *Bacillus subtilis* cellulase gene, resulting in cellulase negative cells. The disruption was performed essentially as described in (Eds. A. L. Sonenshein, J. A. Hoch and Richard Losick (1993) *Bacillus subtilis* and other Gram-Positive Bacteria, American Society for microbiology, p. 618).

Competent cells were prepared and transformed as described by Yasbin, R. E., Wilson, G. A. and Young, F. E. (1975) Transformation and transfection in lysogenic strains of *Bacillus subtilis*: evidence for selective induction of prophage in competent cells. J. Bacteriol, 121:296-304.

General Molecular Biology Methods

Unless otherwise stated all the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for *Bacillus*". John Wiley and Sons, 1990).

Enzymes for DNA manipulations were used according to the manufacturer's instructions (e.g. restriction endonucleases, ligases etc. are obtainable from New England Biolabs, Inc.).

Genomic DNA Preparation

The *Bacillus subtilis* strain used as donor organism was propagated in liquid medium 3 as specified by ATCC (American Type Culture Collection, USA). After 18 hours incubation at 37° C. and 300 rpm, the cells were harvested, and genomic DNA was isolated by the method described by Pitcher et al. [Pitcher, D. G., Saunders, N. A., Owen, R J; Rapid extraction of bacterial genomic DNA with guanidium thiocyanate; *Lett Appl Microbiol* 1989 8 151-156].

Plasmids pMOL995. This plasmid is a pUB110 derivative essentially containing elements making the plasmid propagatable in *Bacillus subtilis*, kanamycin resistance gene and having a strong promoter and the signal peptide cloned from the amyQ gene of *B. amyloliquefaciens* The signal peptide contains a SacII site making it convenient to clone the DNA encoding the mature part of a protein in-fusion with the signal peptide. This results in the expression of a Pre-protein that is directed towards the exterior of the cell.

The plasmid was constructed by means of ordinary genetic engineering and is briefly described in the following.

Description of Plasmid pMOL995:

The pUB110 plasmid (McKenzie, T. et al., 1986, Plasmid 15:93-103) was used as the basis for the construction of pMOL995. In several cloning steps different features were introduced into the NciI restriction site of pUB110.

The features of pMOL995 (SEQ ID NO: 3) are:

Bp 4076-6661 and 1-1962 encodes the pUB110 plasmid.

Bp 1963-2305 encodes Transcriptional terminator from the amyL gene of *B. licheniformis* ATCC14580 plus a few introduced unique restriction sites (EagI, SalI etc.).

Bp 2306-3766 (in reverse) encodes the mature part of the alpha-amylase from WO95/26397 (disclosed as SEQ ID NO: 4 in WO95/26397).

Bp 3767-4075 (in reverse) encodes the Promoter and signal peptide of alpha-amylase cloned from *Bacillus amyloliquefaciens* (used as promoter and described in WO95/10603) plus introduced unique SacI and XmaI site around bp4075 and a unique SacI site around bp3769 for use in later inframe cloning to the signal peptide.

pMOL944. This plasmid is a pUB110 derivative essentially containing elements making the plasmid propagatable in *Bacillus subtilis*, kanamycin resistance gene and having a strong promoter and signal peptide cloned from the amyL gene of *B. licheniformis* ATCC14580. The signal peptide contains a SacII site making it convenient to clone the DNA encoding the mature part of a protein in-fusion with the signal peptide. This results in the expression of a Pre-protein which is directed towards the exterior of the cell.

The plasmid was constructed by means of ordinary genetic engineering and is briefly described in the following.

Construction of pMOL944:

The pUB10 plasmid (McKenzie, T. et al., 1986, Plasmid 15:93-103) was digested with the unique restriction enzyme NciI. A PCR fragment amplified from the amyL promoter encoded on the plasmid pDN1981 (P. L. Jørgensen et al., 1990, Gene, 96, p 37-41.) was digested with NciI and inserted in the NciI digested pUB110 to give the plasmid pSJ2624.

The two PCR primers used have the following sequences:

```
Primer C
                                           (SEQ ID NO: 8)
5'-GTCGCCGGGGCGGCCGCTATCAATTGGTAACTGTATCTCAGC -3'

Primer D
                                           (SEQ ID NO: 9)
5'-GTCGCCCGGGAGCTCTGATCAGGTACCAAGCTTGTCGACCTGCAGAA
TGAGGCAGCAAGAAGAT -3'
```

The Primer C inserts a NotI site in the plasmid.

The plasmid pSJ2624 was then digested with SacI and NotI and a new PCR fragment amplified on amyL promoter encoded on the pDN1981 and synthesized using the primers E and F, was digested with SacI and NotI and this DNA fragment was inserted in the SacI-NotI digested pSJ2624 to give the plasmid pSJ2670.

This cloning replaces the first amyL promoter cloning with the same promoter but in the opposite direction. The two primers used for PCR amplification have the following sequences:

```
Primer E
                                           (SEQ ID NO: 10)
5'-GTCGGCGGCCGCTGATCACGTACCAAGCTTGTCGACCTGCAGAATG
AGGCAGCAAGAAGAT -3'

Primer F
                                           (SEQ ID NO: 11)
5'-GTCGGAGCTCTATCAATTGGTAACTGTATCTCAGC -3'
```

The plasmid pSJ2670 was digested with the restriction enzymes PstI and BclI and a PCR fragment amplified from a cloned DNA sequence encoding the alkaline amylase SP722 (described in WO9526397-A1) using the two primers G and H, was digested with PstI and BclI and inserted to give the plasmid pMOL944. The two primers used for PCR amplification have the following sequence:

```
Primer G
                                           (SEQ ID NO: 12)
5'-AACAGCTGATCACGACTGATCTTTTAGCTTGGCAC -3'

Primer H
                                           (SEQ ID NO: 13)
5'-AACTGCAGCCGCGGCACATCATAATGGGACAAATGGG -3'
```

The primer H inserts a SacII site in the plasmid.

Media

TY (as described in Ausubel, F. M. et al. (eds.) "Current protocols in Molecular Biology". John Wiley and Sons, 1995).

LB agar (as described in Ausubel, F. M. et al. (eds.) "Current protocols in Molecular Biology". John Wiley and Sons, 1995).

LBPG is LB agar supplemented with 0.5% Glucose and 0.05 M potassium phosphate, pH 7.0.

BPX media is described in EP 0 506 780 (WO 91/09129).

The End Point Lyase Assay (at 235 nm), Pectate Units

For determination of the β-elimination an assay measuring the increase in absorbance at 235 nm was carried out using the substrate 1.0% polygalacturonic acid sodium salt (Sigma P-1879) solubilised in 0.1 M EPPS buffer pH 8. Incubation for 20 minutes at 70° C. The reaction is stopped by adding 5 volumes of 0.02 M $H_3PO_4$. For calculation of the catalytic rate an increase of 5.2 Absorbency at 235 units per min corresponds to formation of 1 μmol of unsaturated product (Nasuna and Starr (1966) J. Biol. Chem. Vol 241 page 5298-5306; and Bartling, Wegener and Olsen (1995) Microbiology Vol 141 page 873-881).

One Pectate Unit is the amount of enzyme resulting in formation of one micromole cleaved per minute at pH 8.0 and 70° C.

EXAMPLE 1

Cloning of *Bacillus subtilis* Pectate Lyase Gene

Subcloning and Expression of Mature Pectate Lyase in *B. subtilis*.

The pectate lyase encoding DNA sequence of the invention was PCR amplified using the PCR primer set consisting of these two oligo nucleotides:

```
(Primer A)
                                           SEQ ID NO: 4
5'-CAT TCT GCA GCC GCG GCA GCT GAT TTA GGC CAC CAG
ACG-3'

(Primer B)
                                           SEQ ID NO: 5
5'-GTA CCT CGC GAG TCG ACT TCT TAA TTT AAT TTA CCC
GCA CCC GC-3'
```

Restriction sites SacII and SalI are underlined

The oligonucleotides were used in a PCR reaction in HiFidelity™ PCR buffer (Boehringer Mannheim, Germany), supplemented with 200 μM of each dNTP, 2.6 units of HiFidelity™ Expand enzyme mix and 200 pmol of each primer. Genomic DNA isolated from a strain of the species *Bacillus subtilis* was added as template for the PCR reaction. The genomic DNA was isolated as described above.

The PCR reaction was performed using a DNA thermal cycler (Landgraf, Germany). One incubation at 94° C. for 1 min followed by ten cycles of PCR performed using a cycle profile of denaturation at 94° C. for 15 sec, annealing at 60° C. for 60 sec, and extension at 72° C. for 120 sec, followed by twenty cycles of denaturation at 94° C. for 15 sec, 60° C. for 60 sec and 72° C. for 120 sec (at this elongation step 20 sec are added every cycle). Five-μl aliquots of the amplification product was analysed by electrophoresis in 0.7% agarose gels (NuSieve, FMC). The appearance of a DNA fragment size 1.2 kb indicated proper amplification of the gene segment.

Subcloning of PCR Fragment:

Forty five-μl aliquots of the PCR products generated as described above were purified using QIAquick PCR purification kit (Qiagen, USA) according to the manufacturer's instructions. The purified DNA was eluted in 50 μl of 10 mM Tris-HCl, pH 8.5.

5 μg of pMOL995 and twenty five-μl of the purified PCR fragment was digested with SacII and SalI, electrophoresed in 0.7% agarose gels (NuSieve, FMC), the relevant fragments were excised from the gels, and purified using QIAquick Gel extraction Kit (Qiagen, USA) according to the manufacturer's instructions. The isolated PCR DNA fragment was then ligated to the SacII-SalI digested and purified pMOL995. The ligation was performed overnight at 16° C. using 0.5 μg of each DNA fragment, 1 U of T4 DNA ligase and T4 ligase buffer (Boehringer Mannheim, Germany).

The ligation mixture was used to transform competent *B. subtilis* PL2306. The transformed cells were plated onto LBPG-10 μg/ml of Kanamycin-agar plates. After 18 hours incubation at 37° C. colonies were seen on plates. Several clones were analyzed by isolating plasmid DNA from overnight culture broth.

One such positive clone was re-streaked several times on agar plates as used above, this clone was called MB331. The clone MB331 was grown overnight in TY-10 µg/ml Kanamycin at 37° C., and next day 1 ml of cells were used to isolate plasmid from the cells using the Qiaprep Spin Plasmid Miniprep Kit #27106 according to the manufacturers recommendations for *B. subtilis* plasmid preparations. This DNA was sequenced and revealed a DNA sequence identical to the part of the pectate lyase gene in SEQ ID NO: 1 encoding the mature pectate lyase.

EXAMPLE 2

Expression, Purification and Characterization of *Bacillus subtilis* Pectate Lyase The clone MB331 (deposited as DSM 14218) obtained as described above in Example 1 was grown in 25×200 ml BPX media with 10 µg/ml of Kanamycin in 500 ml baffled shake flasks for 5 days at 37° C. at 300 rpm, whereby 4550 ml of culture broth was obtained. pH was adjusted to 6.1, using acetic acid and 25 ml of cationic agent (C521 10%) and 60 ml of anionic agent (A130 0.1%) was added during agitation for flocculation. The flocculated material was separated by centrifugation using a Sorval RC 3B centrifuge at 10000 rpm for 30 min at 6° C. The resulting supernatant contained a total volume of 3750 ml.

The supernatant was clarified using Whatman glass filters GF/D and C and finally concentrated on a Filtron UF membrane with a cut off of 10 kDa. The total volume of 1500 ml was adjusted to pH 6.0.

For obtaining a highly purified pectate lyase a final step using S-Sepharose cation-exchange chromatography was carried out. 1500 ml of the solution was applied to an 800 ml column containing S-Sepharose (Pharmacia) equilibrated with a buffer of 50 mmol Na-acetate pH 6.0. The pectate lyase bound and was eluted using a 0.5 M NaCl gradient.

Characterization

The pure enzyme constituted a single band in SDS-PAGE of 44 kDa and had an iso-electric point of about 7.6.

The protein concentration was determined using a molar extinction coefficient of 71950 (based on the amino acid composition deducted from the sequence).

The pectate lyase activity could be inhibited by EDTA.

Differential Scanning Calorimetry DSC of the pure enzyme revealed a melting temperature of 58.8° C. at pH 8 in 0.1 M Tris buffer.

EXAMPLE 3

Cloning of *Bacillus subtilis* 168 Pectate Lyase Gene

Subcloning and Expression of Mature Pectate Lyase in *B. subtilis*.

The pectate lyase encoding DNA sequence of the invention was PCR amplified using the PCR primer set consisting of these two oligo nucleotides:

(Primer J)
```
                                                SEQ ID NO: 14
5'-CAT TCT GCA GCC GCG GCA GCT GAT TTA GGC CAC CAG
ACG-3'
```

(Primer K)
```
                                                SEQ ID NO: 15
5'-GTA CCT CGC GAG CGG CCG CTT CTT AAT TTA ATT TAC
CCG CAC CCG C-3'
```

Restriction sites SacII and NotI are underlined

The oligonucleotides were used in a PCR reaction in HiFidelity™ PCR buffer (Boehringer Mannheim, Germany), supplemented with 200 µM of each dNTP, 2.6 units of HiFidelity™ Expand enzyme mix and 200 pmol of each primer. Genomic DNA isolated from a strain of the species *Bacillus subtilis* was added as template for the PCR reaction. The genomic DNA was isolated as described above.

The PCR reaction was performed using a DNA thermal cycler (Landgraf, Germany). One incubation at 94° C. for 1 min followed by ten cycles of PCR performed using a cycle profile of denaturation at 94° C. for 15 sec, annealing at 60° C. for 60 sec, and extension at 72° C. for 120 sec, followed by twenty cycles of denaturation at 94° C. for 15 sec, 60° C. for 60 sec and 72° C. for 120 sec (at this elongation step 20 sec are added every cycle). Five-µl aliquots of the amplification product was analysed by electrophoresis in 0.7% agarose gels (Agarose, SIGMA). The appearance of a DNA fragment size 1.2 kb indicated proper amplification of the gene segment.

Subcloning of PCR Fragment:

Forty five-µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5.

5 µg of pMOL944 and twenty five-µl of the purified PCR fragment was digested with SacII and SalI, electrophoresed in 0.7% agarose gels (NuSieve, FMC), the relevant fragments were excised from the gels, and purified using QIAquick Gel extraction Kit (Qiagen, USA) according to the manufacturer's instructions. The isolated PCR DNA fragment was then ligated to the SacII-SalI digested and purified pMOL944. The ligation was performed overnight at 16° C. using 0.5 µg of each DNA fragment, 1 U of T4 DNA ligase and T4 ligase buffer (Boehringer Mannheim, Germany).

The ligation mixture was used to transform competent *B. subtilis* PL1801. The transformed cells were plated onto LBPG-10 µg/ml of Kanamycin-agar plates. After 18 hours incubation at 37° C. colonies were seen on plates. Several clones were analyzed by isolating plasmid DNA from overnight culture broth.

One such positive clone was re-streaked several times on agar plates as used above, this clone was called MB1306. The clone MB1306 was grown overnight in TY-10 µg/ml Kanamycin at 37° C., and next day 1 ml of cells were used to isolate plasmid from the cells using the Qiaprep Spin Plasmid Miniprep Kit #27106 according to the manufacturers recommendations for *B. subtilis* plasmid preparations. This DNA was sequenced and revealed a DNA sequence identical to the part of the pectate lyase gene in SEQ ID NO: xx encoding the mature pectate lyase.

EXAMPLE 4

Expression of the Pectate Lyase from *B. subtilis* 168

The clone MB1306 obtained as described above in Example 3 was grown in 25×200 ml BPX media with 10 µg/ml of Kanamycin in 500 ml baffled shake flasks for 5 days at 37° C. at 300 rpm, whereby 4550 ml of culture broth was obtained.

EXAMPLE 5

Cloning of *Bacillus subtilis* DSM 14979 Pectate Lyase Gene

The pectate lyase encoding DNA sequence from *Bacillus subtilis* DSM 14979 was PCR amplified using the PCR primer set consisting of the following oligonucleotides:

(Primer L)
```
                                                SEQ ID NO:16
5'-CAT TCT GCA GCC GCG GCA GCT GAT TTA GGC CAC CAG
ACG-3'
```

-continued (Primer M)
SEQ ID NO:17
5'-GTA CCT CGC GAG CGG CCG CTT CTT AAT TTA ATT TAC CCG CAC CCG C-3'

Restriction sites SacII and NotI are underlined.

50 pmol of each of the oligonucleotides was used in a PCR reaction in PCR buffer (10 mM Tris-HCl, pH 8.3, 50 mM KCl) containing 200 µM of each dNTP, 3.5 mM MgCl2, 2.5 Units AmpliTaq Gold™ (Perkin-Elmer), and approximately 100 to 200 ng genomic DNA, used as template for PCR amplification. Genomic DNA was isolated as described above. The total volume was 50 µl. The PCR reactions were carried out in a Perkin-Elmer GeneAmp PCR System 2400.

The PCR reaction was carried out using a cycle profile of:

94° C.–10 min; 1 cycle

94° C.–1 min, 55° C.–30 sec, 72° C.–1 min 30 sec; 25 cycles

72° C.–7 min; 1 cycle

5 µl aliquots of the amplification products were analysed by electrophoresis in 1.0% agarose gels (Agarose, SIGMA). The appearance of a DNA fragment size 1.2 kb indicated proper amplification of the gene segment. Sequencing of the fragment revealed the DNA sequence shown in SEQ ID NO:18, which encodes the mature pectate lyase (shown in SEQ ID NO:19) from *B. subtilis* DSM 14979.

EXAMPLE 6

Measuring the Stability of Pectate Lyase in Liquid Detergent

The detergent stability of the pectate lyase variants of the present invention is assessed by measuring the activity of the variants after incubation of an enzyme-detergent mixture, which is described below.

Residual Activity Assay 30 micro liter of an enzyme solution (culture supernatant or purified enzyme) is mixed with 1 ml of a typical European or US heavy duty liquid detergent in two sample tubes. One of the tubes is stored on ice while the other is incubated at 40 degrees Celsius for 90 minutes. As reference 30 micro liter water is mixed with 1 ml of detergent and incubated on ice.

After incubation, 9 ml of ice-cold water is added to the samples, which are mixed vigorously and stored on ice until further analysis.

The enzymatic activity is measured by first mixing 50 micro liter of enzyme-detergent mixture with 5 ml of assay buffer (100 mM Tris-HCL, 0.68 mM $CaCl_2$, pH 8.0), secondly from which solution, 75 micro liter is mixed with 75 micro liter freshly prepared substrate solution (1% polygalactoronic acid in assay buffer) and incubated at 40 degrees Celsius for 10 minutes. Thirdly, 100 micro liter of the incubation mixture is added into 100 micro liter stop-buffer (50 mM $H_3PO_4$) in a UV-transparent microtiter plate and the absorbance at 235 nm is measured in a spectofotometer. The water-detergent sample is used to zero the spectofotometer.

Now the residual activity is calculated as the activity (A235 absorbance) in the sample incubated at 40 degrees Celsius for 90 minutes relative to the activity in the sample stored on ice:

Residual activity (RA)=Absorbance [sample incubated at 40 degrees Celsius]/Absorbance [sample incubated at 0 degrees Celsius]

Thus, the residual activity is equivalent to the detergent stability of the enzyme. FIG. 1 lists the improved residual activity of a number of substitutions of the MB331 pectate lyase incubated in a typical European heavy duty liquid detergent. The majority of the substitutions give rise to more than 50% improvement of the detergent stability of the parent pectate lyase. Equivalently the substitutions of the MB331 pectate lyase listed in FIG. 2 significantly improve the stability of the enzyme when incubated in a typical US heavy duty liquid detergent.

| Mutations | Residual activity | Residual activity in % of parent enzyme |
|---|---|---|
| Pectate lyase of SEQ ID NO:2 (parent enzyme) | 23 | 100 |
| Q40E | 28 | 121.7 |
| F251I | 30 | 130.4 |
| A332P | 31 | 134.8 |
| L106Q | 31 | 134.8 |
| R272H | 31 | 134.8 |
| R272Y | 31 | 134.8 |
| A91E | 33 | 143.5 |
| K115I + K213E | 33 | 143.5 |
| K139I + K213N | 33 | 143.5 |
| H5R + K257N + S302A | 34 | 147.8 |
| K139M | 34 | 147.8 |
| K87A | 34 | 147.8 |
| D48P | 35 | 152.2 |
| K99I + I196V | 35 | 152.2 |
| T105P | 35 | 152.2 |
| K115A + K115A | 36 | 156.5 |
| K115A + K118A + M122N | 36 | 156.5 |
| K115Q | 36 | 156.5 |
| K213T | 36 | 156.5 |
| V141E + C199S + K213E | 36 | 156.5 |
| K115I + Q146H | 37 | 160.9 |
| K257N | 37 | 160.9 |
| K71E + K118E | 38 | 165.2 |
| S331P | 38 | 165.2 |
| T49P + N156S | 38 | 165.2 |
| K314N + S340P | 39 | 169.6 |
| V141E + I235V | 39 | 169.6 |

-continued

| Mutations | Residual activity | Residual activity in % of parent enzyme |
|---|---|---|
| G46D + K257N | 40 | 173.9 |
| Q146H | 40 | 173.9 |
| A305P | 41 | 178.3 |
| K218P | 41 | 178.3 |
| S28T + S30F + K334E + N363S | 41 | 178.3 |
| D48E + L106Q + I140V + F215Y + K218E | 42 | 182.6 |
| H193Y + S256C + V389I + A393V | 42 | 182.6 |
| R272C | 42 | 182.6 |
| E9G + H31N + N50D + L106Q + A111E + T136S + V141L + F201L + N202K + F215Y + G286A + A381D + H384N | 43 | 187.0 |
| K213N + T258I | 43 | 187.0 |
| E9G + H31N + L106Q + D303S + A305P + T335S + H384N + S391N | 44 | 191.3 |
| E9G + H31N + D48E + L106Q + A111E + S301Y + D303S + A305P + T378S + H384N + S391N | 45 | 195.7 |
| L45V + N50Y + N185H | 46 | 200.0 |
| N11Y + K87E + K99N | 46 | 200.0 |
| E9G + D48E + L106Q + S316F + A381D | 48 | 208.7 |
| S30P + K115I + K139I + Q146H + S337C | 49 | 213.0 |
| E9G + H31N + D48E + L106Q + I140V + F215Y + D303S + A305P + T378S + H384N + S391N | 51 | 221.7 |
| H31N + T105A + L106Q + A111E + V141L + K218E + D303S + A305P + D326N + T335S + H384N + S391N | 51 | 221.7 |
| K26Q + K47N + L106Q + I140V + F215Y + D303S + A305P + T378S + H384N + S391N | 53 | 230.4 |
| D48E + L106Q + I140V + F215Y + D303S + A305P + T378S + H384N + S391N | 56 | 243.5 |
| K213N | 60 | 260.9 |
| K213T + K218L + A305P | 64 | 278.3 |
| S337C | 65 | 282.6 |
| M64F + K213T + K218L + A305P | 70 | 304.3 |
| M64F + M122K + K118E + K213T + K218L + A305P | 71 | 308.7 |
| K139I + Q146H + S337C | 74 | 321.7 |
| K139I + Q146H + K257N + S337C | 75 | 326.1 |
| M64F + K139I + Q146H + S337C | 90 | 391.3 |

| Mutations | Residual activity | Residual activity in % of parent enzyme |
|---|---|---|
| Pectate lyase of SEQ ID NO:2 (parent enzyme) | 45 | 100 |
| R272Y | 50 | 111.1 |
| M237I | 51 | 113.3 |
| C199N | 51 | 113.3 |
| F215Y | 52 | 115.6 |
| K213T | 52 | 115.6 |
| A228I + F251I | 53 | 117.8 |
| K115I + Q146H | 57 | 126.7 |
| K257N | 59 | 131.1 |
| K213N + T258I | 60 | 133.3 |
| M122Q | 61 | 135.6 |
| K218P | 61 | 135.6 |
| K386P | 61 | 135.6 |
| A332P | 62 | 137.8 |
| F251I | 64 | 142.2 |
| A305P | 64 | 142.2 |
| D48P | 64 | 142.2 |
| S134L + K257E | 66 | 146.7 |
| S331P | 75 | 166.7 |
| K139I + Q146H + S337C | 100 | 222.2 |

WASH PERFORMANCE EXAMPLES

Wash Performance Example A

Pectate Lyase of the Invention in Full Scale.

The pectate lyase (SEQ ID NO:2) from clone MB331 (hereinafter denoted the MB331 enzyme) was evaluated in full scale wash in a European heavy duty liquid detergent using a range of different test swatches. The enzyme level used was 0.05 mg MB331 enzyme per liter wash water. Very high wash performance on many different fruit or vegetable based stains was found at this dosage level as shown in the table below.

| Swatch | Delta Remission |
|---|---|
| Bilberry Jam | 15.0 |
| Avocado | 14.9 |
| Tomato concentrate | 13.3 |
| Ketchup | 10.6 |
| Banana | 8.4 |
| Tomato puree | 7.3 |
| Pear | 7.2 |
| Apple | 5.6 |
| Prune | 5.5 |
| Blackberries | 4.8 |
| Carrot juice | 3.3 |

Method Description

The following equipment and wash conditions were used.

Washer: AEG Økolavamat 86820 update

Wash programme: 40° C. short wash

Detergent: 5 g/l European heavy duty liquid detergent

Water hardness: 15°dH (4:1 Ca/Mg; 2.14 mM CaCl$_2$ and 0.54 mM MgCl$_2$)

Enzyme: 0.05 mg MB331 pectate lyase protein per liter wash water

Swatches: Pre-made food-stains from Equest

Evaluation: Remission was measured at 460 nm on a Elrepho 2000 Remission Spectrophotometer. Delta remission is calculated as:

$R_{enzyme} - R_{no\ enzyme}$, where R is the remission at 460 nm.

Wash Performance Example B

Wash Performance of Pectinases on Banana Swatches in Small Scale Wash

The pectate lyase (SEQ ID NO:2) from clone MB331 was compared to other pectate lyases in a European heavy duty liquid detergent in a small scale wash assay using a Launderometer and banana swatches. The results are shown in the table below, where the wash performance effect of MB331 is adjusted to 100%.

Best wash performance is observed by the two *Bacillus subtilis* pectate lyases from DSM14218 (SEQ ID NO:2 from clone MB331) and from *B. subtilis* A168 (SEQ ID NO:7 from clone MB1306), whereas the pectate lyases from *B. licheniformis* (SP958) and *B. agaradherens* (SP956) show less than 50% performance.

| Enzyme class | Enzyme | Wash performance |
| --- | --- | --- |
| Pectate lyase | *B. subtilis* MB331 | 100% |
| Pectate lyase | *B. subtilis* A168, MB1306 | 97% |
| Pectate lyase | *B. licheniformis* (SEQ ID NO: 4 in WO99/27084) | 43% |
| Pectate lyase | *B. agaradherens* (SEQ ID NO: 2 in WO99/27084) | 36% |

Method Description

Preparation of banana swatches: Three bananas were mashed and homogenised in a blender for 3-4 minutes with 70 ml deionised water. The suspension were poured into a tray and stored for about 2 hours. Clean cotton swatches (style 400 from Testfabrics Inc.) were soaked in the solution, squeezed between two rolls and dried overnight.

Wash performance assay: Banana swatches were washed in a European heavy duty liquid detergent and 15° dH water (4:1 Ca/Mg) using a Launder-ometer. The water hardness was adjusted by addition of $CaCl_2$ (2.14 mM) and $MgCl_2$ (0.54 mM). Each beaker (500 ml) was added 20 steel balls, 200 ml detergent solution, 0.05 mg/l pectinase and 3 banana swatches (5 cm×5 cm). The wash programme was 10 minutes heat-up from 25° C. to 40° C. followed by 20 minutes wash at 40° C. The swatches were rinsed in tap water and dried at room temperature overnight.

Evaluation: Remission of the swatches was measured at 440 nm using a MacBeth ColorEye 7000 remission spectrophotometer.

Wash Performance Example C

MB331 Variants with Improved Stability in Liquid Detergent

Variants of the MB331 pectate lyase with improved stability in heavy duty liquid detergent have been created. The stability was determined by storage for 7 days at 35° C. of the pectate lyase in the liquid detergent followed by wash performance evaluation in a Launderometer assay using banana swatches. The table below shows strong improvement in storage stability of 4 different MB331 variants. The wash performance is unchanged for MB331-var147 and 168, whereas the wash performance of MB331-var135 and 137 is slightly lower than the wash performance of MB331.

| MB331 variant | Storage stability | Wash performance |
| --- | --- | --- |
| Wildtype | 0% | 100% |
| M64F + K139I + Q146H + S337C | 74% | 68% |
| M64F + V123I + K139I + Q146H + S337C | 74% | 79% |
| K139N + E158N + Q146H + S337C | 57% | 101% |
| M64F + M237I + K139I + Q146H + S337C | 59% | 94% |

Method Description

The pectinases were incubated in a European heavy duty liquid detergent on a water bath at 35° C. for 7 days. Samples of stored and fresh enzymes were tested in the Launderometer wash performance assay described in wash performance example B above using banana stains purchased from Equest and 0.01 mg/l pectinase. The wash performance of fresh MB331 is adjusted to 100%. The storage stability is measured as % residual wash performance after 7 days storage compared to fresh enzyme.

DETERGENT EXAMPLES

Detergent Example I

Granular fabric detergent compositions in accordance with the invention may be prepared as follows:

| | A | B | C |
| --- | --- | --- | --- |
| LAS | 6.5 | 8.0 | 8.0 |
| Sodium sulfate | 15.0 | 20.0 | 20.0 |
| Zeolite A | 26.0 | 20.0 | 25.0 |
| Sodium nitrilotriacetate | 5.0 | — | 2.0 |
| Enzyme of the invention | 0.01 | 0.001 | 0.05 |
| PVP | 0.5 | — | 0.5 |
| TAED | 3.0 | — | 2.0 |
| Boric acid | 4.0 | — | — |
| PB1 | 18.0 | 15.00 | 15.00 |
| NACA-OBS | — | — | 1.0 |
| Metal catalyst | 0.02 | — | — |
| Phenol sulphonate | 0.1 | — | — |
| Minors (Other Enzymes, brighteners, perfumes, dyes, . . . ) | Up to 100 | | |

Detergent Example II

Compact granular fabric detergent composition (density 800 g/l) in accordance with the invention may be prepared as follows:

| | A | B |
| --- | --- | --- |
| 45AS | 8.0 | 8.0 |
| 25E3S | 2.0 | 2.0 |
| 25E5 | 3.0 | 3.0 |
| 25E3 | 3.0 | 3.0 |
| TFAA | 2.5 | 2.5 |

-continued

|  | A | B |
|---|---|---|
| Zeolite A | 17.0 | 17.0 |
| NaSKS-6 | 12.0 | 12.0 |
| Citric acid | 3.0 | 3.0 |
| Carbonate | 7.0 | 7.0 |
| MA/AA | 5.0 | 5.0 |
| CMC | 0.4 | 0.4 |
| Enzymes | 0.05 | 0.05 |
| Enzyme of the invention | 0.01 | 0.001 |
| TAED | 6.0 | 6.0 |
| Percarbonate | 22.0 | 22.0 |
| EDDS | 0.3 | 0.3 |
| Granular suds suppressor | 3.5 | 3.5 |
| Water/minors (brighteners, perfumes, dyes, . . . ) | Up to 100% | |

Detergent Example III

Granular fabric detergent composition in accordance with the invention, which is especially useful in the laundering of coloured fabrics, was prepared as follows:

|  | A | B |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme of the invention | 0.10 | 0.05 |
| Silicate | 2.5 | — |
| Sulphate | 5.2 | 3.0 |
| PVP | 0.5 | — |
| PVPVI | — | 0.2 |
| PB1 | 1.0 | — |
| Phenol sulfonate | 0.2 | — |
| Water/Minors | Up to 100% | |

Detergent Example IV

Granular fabric detergent compositions in accordance with the invention which provide "Softening through the wash" capability may be prepared as follows:

|  | A | B |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| PB1 | 15.0 | — |
| Percarbonate | — | 15.0 |

|  | A | B |
|---|---|---|
| TAED | 5.0 | 5.0 |
| Smectite clay | 10.0 | 10.0 |
| HMWPEO | — | 0.1 |
| Enzyme of the invention | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

Detergent Example V

The following laundry composition, which may be in the form of a granule or a tablet, was prepared according to the present invention.

| Base Product | A | B | C | D | E |
|---|---|---|---|---|---|
| C45 AS/TAS | 8.0 | 5.0 | 3.0 | 3.0 | 3.0 |
| LAS | 8.0 | — | 8.0 | — | 7.0 |
| C25AE3S | 0.5 | 2.0 | 1.0 | — | — |
| C25AE5/AE3 | 2.0 | — | 5.0 | 2.0 | 2.0 |
| QAS | — | — | — | 1.0 | 1.0 |
| Zeolite A | 20.0 | 18.0 | 11.0 | — | 10.0 |
| SKS-6 (I) (dry add) | — | — | 9.0 | — | — |
| MA/AA | 2.0 | 2.0 | 2.0 | — | 4.0 |
| Citrate | — | 2.0 | — | — | — |
| Citric acid | 2.0 | — | 1.5 | 2.0 | — |
| DTPA | 0.2 | 0.2 | — | — | — |
| EDDS | — | — | 0.5 | 0.1 | — |
| HEDP | — | — | 0.2 | 0.1 | — |
| PB1 | 3.0 | 5.0 | 10.0 | — | 4.0 |
| Percarbonate | — | — | — | 18.0 | — |
| NOBS | 3.0 | 4.0 | — | — | 4.0 |
| NACA OBS | — | — | 2.0 | — | — |
| TAED | — | — | 2.0 | 5.0 | — |
| Metal catalyst | — | 0.02 | — | — | — |
| Carbonate | 15.0 | 18.0 | 8.0 | 15.0 | 15.0 |
| Sulphate | 5.0 | 12.0 | 2.0 | 17.0 | 3.0 |
| Silicate | — | 1.0 | — | — | 8.0 |
| Enzymes | 0.04 | 0.04 | 0.04 | 0.06 | 0.04 |
| Enzyme of the invention | 0.001 | 0.002 | 0.02 | 0.05 | 0.005 |
| Moisture and miscellaneous | Up to 100% | | | | |

Detergent Example VI

The following granular detergent was prepared in accordance with the present invention:

|  | A | B | C | D | E | F | G | H |
|---|---|---|---|---|---|---|---|---|
| Base granule | | | | | | | | |
| STPP | — | 22.0 | — | 15.0 | — | 22.0 | — | 15.0 |
| Zeolite A | 30.0 | — | 24.0 | 5.0 | 30.0 | — | 24.0 | 5.0 |
| Sulfate | 5.5 | 5.0 | 7.0 | 7.0 | 5.5 | 5.0 | 7.0 | 7.0 |
| MA/AA | 3.0 | 12 | — | 6.0– | 3.0 | 12.0 | 2.0 | 6.0 |
| LAS | 14.0 | 10.0 | 9.0 | 20.0 | 14.0 | 10.0 | 9.0 | 20.0 |
| C45AS | 8.0 | 7.0 | 9.0 | 7.0 | 8.0 | 7.0 | 9.0 | 7.0 |
| C45AE11S | — | 1.0 | — | 1.0 | — | 1.0 | — | 1.0 |
| MES | 0.5 | 4.0 | 6.0 | — | 0.5 | 4.0 | 6.0 | — |
| SADS | 2.5 | — | — | 1.0 | 2.5 | — | — | 1.0 |
| Silicate | — | 1.0 | 0.5 | 10.0 | — | 1.0 | 0.5 | 10.0 |
| Soap | — | 2.0 | — | — | — | 2.0 | — | — |
| Brightener | 0.2 | 0.2 | 0.2 | 0.2 | 0.2 | 0.2 | 0.2 | 0.2 |
| Carbonate | 6.0 | 9.0 | 8.0 | 10.0 | 6.0 | 9.0 | 8.0 | 10.0 |
| PEG 4000 | — | 1.0 | 1.5 | — | — | 1.0 | 1.5 | — |
| DTPA | — | 0.4 | — | — | — | 0.4 | — | — |
| Spray on | | | | | | | | |
| C25E9 | — | — | — | 5.0 | — | — | — | 5.0 |
| C45E7 | 1.0 | 1.0 | — | — | 1.0 | 1.0 | — | — |
| C23E9 | — | 1.0 | 2.5 | — | — | 1.0 | 2.5 | — |
| Perfume | 0.2 | 0.3 | 0.3 | — | 0.2 | 0.3 | 0.3 | — |
| Dry additives | | | | | | | | |
| Carbonate | 5.0 | 10.0 | 13.0 | 8.0 | 5.0 | 10.0 | 13.0 | 8.0 |
| PVPVI/PVNO | 0.5 | — | 0.3 | — | 0.5 | — | 0.3 | — |
| Enzymes | 0.04 | 0.03 | 0.03 | .04 | 0.04 | 0.03 | 0.03 | 0.01 |
| Enzyme of the invention | 0.001 | 0.02 | 0.03 | 0.015 | 0.001 | 0.02 | 0.03 | 0.015 |
| DTPA | 0.5 | 0.3 | 0.5 | 1.0 | 0.5 | 0.3 | 0.5 | 1.0 |
| PB1 | 5 | 3.0 | 10 | 4.0 | 5 | 3.0 | 10 | 4.0 |
| NOBS/TAED | 0.5 | 0.3 | 0.5 | 0.6 | 0.5 | 0.3 | 0.5 | 0.6 |
| Sulfate | 4.0 | 5.0 | — | 5.0 | 4.0 | 5.0 | — | 5.0 |
| SRP | — | 0.4 | — | — | — | 0.4 | — | — |
| Granular Sud supressor | — | 0.5 | — | — | — | 0.5 | — | — |
| speckle | 0.9 | — | 2.7 | 1.2 | 0.9 | — | 2.7 | 1.2 |
| Moisture and miscellaneous | | | | Up to 100% | | | | |

Detergent Example VII

The following liquid detergent formulations were prepared according to the present invention:

|  | A | B | C | D | E |
|---|---|---|---|---|---|
| LAS | 11.5 | 9.0 | — | 4.0 | — |
| C25E2.5S | — | 3.0 | 18.0 | — | 16.0 |
| C45E2.25S | 11.5 | 3.0 | — | 16.0 | — |
| C23E9 | — | 3.0 | 2.0 | 2.0 | 1.0 |
| C23E7 | 3.2 | — | — | — | — |
| CFAA | — | — | 5.0 | — | 3.0 |
| TopPalmKernel Fatty Acid | 2.0 | — | 2.0 | 0.5 | 2.0 |
| Citric (50%) | 6.5 | 1.0 | 2.5 | 4.0 | 2.5 |
| Ca and/or Ca formate | 0.6 | 0.7 | 0.2 | 0.05 | 0.05 |
| SCS | 4.0 | 1.0 | 3.0 | 1.2 | — |
| Borate | 0.6 | — | 3.0 | 2.0 | 3.0 |
| Na hydroxide | 6.0 | 2.0 | 3.5 | 4.0 | 3.0 |
| Ethanol | 2.0 | 1.0 | 4.0 | 4.0 | 3.0 |
| 1,2 Propanediol | 3.0 | 2.0 | 8.0 | 8.0 | 5.0 |
| Monoethanolamine | 3.0 | 1.5 | 1.0 | 2.5 | 1.0 |
| TEPAE | 2.0 | — | 1.0 | 1.0 | 1.0 |
| Enzyme of the invention | 0.001 | 0.002 | 0.01 | 0.01 | 0.005 |
| Enzymes | 0.03 | 0.01 | 0.03 | 0.02 | 0.02 |
| SRP | 0.2 | — | 0.1 | — | — |
| DTPA | — | — | 0.3 | — | — |
| PVNO | — | — | 0.3 | — | 0.2 |
| Brightener | 0.2 | 0.07 | 0.1 | — | — |
| Suds suppressor | 0.04 | 0.02 | 0.1 | 0.1 | 0.1 |
| Miscellaneous and water | | | | | |

Detergent Example VIII

Heavy-duty liquid fabric detergent compositions in accordance with the invention may be prepared as follows:

|  | A | B |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme of the invention | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

Detergent Example IX

Heavy-duty liquid fabric detergent compositions in accordance with the invention may be prepared as follows:

|  | A | B | C |
|---|---|---|---|
| C25AES | 18.0 | 15.0 | 14.0 |
| LAS | 5.8 | 5.0 | 4.0 |
| C810 Amine | 1.4 | 2.0 | — |
| NI 24-7 | 2.8 | 2.0 | 3.0 |
| Citric acid | 2.5 | 3.0 | 3.0 |
| Fatty acid | 8.5 | 3.0 | 3.0 |
| Enzymes | 0.02 | 0.02 | 0.006 |
| Boric acid | 2.0 | 2.0 | 2.0 |
| Ethoxylate tetraethylene pentaimine | 0.9 | 1.0 | 1.0 |
| Polyethylene imine etoxylated | 0.7 | — | 1.0 |
| DETPMP | 0.3 | — | — |
| HEDP | 0.35 | — | — |
| Ethanol | 1.0 | 3.0 | 3.0 |
| 1,2,propanediol | 8.0 | 4.0 | 5.0 |
| MEA | 9.8 | 2.0 | 2.0 |
| NaCS | 2.0 | — | — |
| Suds suppressors | 0.25 | 0.01 | 0.01 |
| Minors (perfumes, brighteners, etc) and water | Up to 100% | | |

Detergent Example X

The following illustrates detergent tablets of the present invention suitable for use in a dishwashing machine.

|  | A | B | C | D | E | F |
|---|---|---|---|---|---|---|
| Phase 1 | | | | | | |
| STPP | 5.0 | 9.6 | 10.0 | 7.10 | 6.0 | 11.5 |
| Silicate | 1.7 | 0.67 | 1.6 | 1.0 | 1.0 | 2.4 |
| SKS-6 | 2.5 | 1.5 | — | 2.3 | 2.25 | — |
| Carbonate | 5.00 | 2.74 | 3.5 | 3.59 | 4.10 | 5.25 |
| HEDP | 0.25 | 0.18 | 0.18 | 0.28 | 0.28 | 0.28 |
| PB1 | 3.5 | 2.45 | 2.45 | 3.68 | 3.68 | 3.68 |
| PAAC | 0.002 | 0.002 | 0.002 | 0.003 | 0.004 | 0.004 |
| Citrate | — | 0.5 | — | 0.2 | — | — |
| Cellulose | — | — | 0.65 | 0.8 | — | — |
| Enzymes | 0.01 | 0.008 | 0.008 | 0.02 | 0.01 | 0.01 |
| Nonionic | 0.90 | 0.80 | 0.80 | 1.20 | 1.20 | 1.20 |
| PEG 4000 | 0.4 | 0.36 | 0.26 | 0.38 | 0.39 | 0.39 |
| BTA | 0.01 | 0.04 | 0.04 | — | 0.06 | 0.06 |
| Paraffin | 0.16 | 0.17 | 0.10 | 0.15 | 0.15 | 0.15 |
| Perfume | 0.02 | 0.02 | 0.02 | 0.013 | 0.013 | 0.013 |
| Sulphate | — | — | — | 0.502 | 0.05 | 2.838 |
| Total | 19.65 g | 19.7 g | 19.77 g | 21.54 g | 19.43 g | 28.0 g |
| Phase 2 | | | | | | |
| Enzymes | 0.03 | 0.03 | 0.03 | 0.03 | 0.03 | 0.03 |
| Enzyme of the invention | 0.01 | 0.02 | 0.005 | 0.001 | 0.003 | 0.005 |
| Citric acid and/or Citrate | 0.3 | 0.20 | 0.3 | 0.3 | 0.20 | 0.3 |
| Sulphamic acid | — | 0.30 | — | — | 0.30 | — |
| Bicarbonate | 0.92 | 0.25 | 0.45 | 1.09 | 0.30 | 0.45 |
| Carbonate | — | 0.55 | — | — | 0.55 | — |
| Silicate | — | — | 0.64 | — | — | 0.64 |
| $CaCl_2$ | — | 0.07 | — | — | 0.07 | — |
| PEG 400 | 0.15 | — | — | — | — | — |
| PEG 4000 | 0.08 | 0.06 | 0.06 | 0.06 | 0.06 | 0.06 |
| Total | 2.0 g | 2.0 g | 2.0 g | 2.0 g | 2.0 g | 2.0 g |

Detergent Example XI

The following illustrates a liquid detergent composition of the present invention suitable for use in a dishwashing machine:

|  | Example | | | | |
|---|---|---|---|---|---|
|  | A | B | C | D | E |
| KOH | 14.3 | 14.3 | 14.3 | 11.4 | 4.7 |
| $H_2SO_4$ | 11.3 | 11.3 | 11.3 | 9.00 | — |
| STPP | 16.00 | 16.00 | 16.00 | 20.00 | — |
| SKTP | — | — | — | — | 30.00 |
| 1,2-Propanediol | 0.50 | 0.50 | 0.50 | 0.5 | 6.00 |
| Boric acid | 3.00 | 3.00 | 3.00 | 3.0 | 4.00 |
| Polygel premix | 24.40 | 24.40 | 24.40 | 24.00 | 24.40 |
| PVPVI | 0.02 | — | — | — | — |
| SLF18 | 1.0 | — | 1.0 | 1.00 | — |
| $C_{16}$ Amine Oxide | 0.6 | 0.6 | — | 2.00 | 2.00 |
| ACNI | 0.3 | 0.3 | — | — | 3.00 |
| $CaCl_2$ | 0.04 | 0.04 | 0.04 | 0.4 | 0.4 |
| Na benzoate | 0.6 | 0.6 | 0.6 | 0.6 | 0.6 |
| Preservative | 0.05 | 0.05 | 0.05 | 0.05 | 0.05 |
| Enzymes | 0.06 | 0.03 | 0.03 | 0.03 | 0.03 |
| Enzyme of the present invention | 0.03 | 0.015 | 0.02 | 0.02 | 0.01 |
| Water and minors | to 100% | | | | |

| 0-1 | Form - PCT/RO/134 (EASY) Indications Relating to Deposited Microorganism(s) or Other Biological Material (PCT Rule 13bis) | |
|---|---|---|
| 0-1-1 | Prepared using | PCT-EASY Version 2.92 (updated Jan. 01, 2002) |
| 0-2 | International Application No. | |
| 0-3 | Applicant's or agent's file reference | 10171-WO |
| 1 | The indications made below relate to the deposited microorganism(s) or other biological material referred to in the description on: | |
| 1-1 | page | 3 |
| 1-2 | line | 27 |
| 1-3 | Identification of Deposit | |
| 1-3-1 | Name of depositary institution | DSMZ-Deutsche Sammlung von Mikroorganismen und Zellkulturen GmbH |
| 1-3-2 | Address of depositary institution | Mascheroder Weg 1b, D-38124 Braunschweig, Germany |
| 1-3-3 | Date of deposit | 05 Apr. 2001 (05.04.2001) |
| 1-3-4 | Accession Number | DSMZ 14218 |
| 1-4 | Additional Indications | NONE |
| 1-5 | Designated States for Which Indications are Made | all designated States |
| 1-6 | Separate Furnishing of indications These indications will be submitted to the International Bureau later | NONE |
| 2 | The indications made below relate to the deposited microorganism(s) or other biological material referred to in the description on: | |
| 2-1 | page | 57 |
| 2-2 | line | 23 |
| 2-3 | Identification of Deposit | |
| 2-3-1 | Name of depositary institution | DSMZ-Deutsche Sammlung von Mikroorganismen und Zellkulturen GmbH |
| 2-3-2 | Address of depositary institution | Mascheroder Weg 1b, D-38124 Braunschweig, Germany |
| 2-3-3 | Date of deposit | 03 May 2002 (03.05.2002) |
| 2-3-4 | Accession Number | DSMZ 14979 |
| 2-4 | Additional Indications | NONE |
| 2-5 | Designated States for Which Indications are Made | all designated States |
| 2-6 | Separate Furnishing of Indications These indications will be submitted to the International Bureau later | NONE |

The invention claimed is:

1. An isolated pectate lyase comprising the sequence of amino acids 1-399 of SEQ ID NO: 2.

2. The pectate lyase of claim 1, consisting of the sequence of amino acids 1-399 of SEQ ID NO: 2.

3. A detergent composition comprising
   (a) a surfactant and
   (b) a pectate lyase comprising the sequence of amino acids 1-399 of SEQ ID NO: 2.

4. The detergent composition of claim 3, wherein the pectate lyase consists of the sequence of amino acids 1-399 of SEQ ID NO: 2.

5. The detergent composition of claim 3, wherein the pectate lyase is present at a level of from 0.0001% to 2% pure enzyme by weight of total composition.

6. The detergent composition of claim 3, which further comprises one or more enzymes selected from the group consisting of proteases, cellulases (endoglucanases), beta-glucanases, hemicellulases, lipases, peroxidases, laccases, alpha-amylases, glucoamylases, cutinases, pectinases, reductases, oxidases, phenoloxidases, ligninases, pullulanases, pectate lyases, xyloglucanases, xylanases, pectin acetyl esterases, polygalacturonases, rhamnogalacturonases, pectin lyases, mannanases, pectin methylesterases, cellobiohydrolases, transglutaminases; and mixtures thereof.

7. The detergent composition of claim 3, wherein the surfactant is an anionic surfactant and is present at a level up to 30% by weight.

8. The detergent composition of claim 3, which further comprises a bleaching agent.

9. A method of cleaning a fabric, dishware or hard surface, comprising treating the fabric, dishware or hard surface with a detergent composition of claim 3.

* * * * *

UNITED STATES PATENT AND TRADEMARK OFFICE
CERTIFICATE OF CORRECTION

PATENT NO. : 7,611,882 B2 Page 1 of 1
APPLICATION NO. : 10/478840
DATED : November 3, 2009
INVENTOR(S) : Bjørnvad et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 143 days.

Signed and Sealed this

Twelfth Day of October, 2010

David J. Kappos
*Director of the United States Patent and Trademark Office*